US008679479B2

(12) United States Patent
Georgiou et al.

(10) Patent No.: US 8,679,479 B2
(45) Date of Patent: Mar. 25, 2014

(54) METHODS FOR PURIFYING PEGYLATED ARGINASE

(75) Inventors: George Georgiou, Austin, TX (US); Everett Stone, Austin, TX (US)

(73) Assignee: AERase, Inc., Austin, TX (US)

( * ) Notice: Subject to any disclaimer, the term of this patent is extended or adjusted under 35 U.S.C. 154(b) by 0 days.

(21) Appl. No.: 13/380,776

(22) PCT Filed: Jun. 28, 2010

(86) PCT No.: PCT/US2010/040205
§ 371 (c)(1),
(2), (4) Date: Mar. 28, 2012

(87) PCT Pub. No.: WO2011/008495
PCT Pub. Date: Jan. 20, 2011

(65) Prior Publication Data
US 2012/0177628 A1    Jul. 12, 2012

Related U.S. Application Data

(60) Provisional application No. 61/221,396, filed on Jun. 29, 2009.

(51) Int. Cl.
*A61K 38/46*     (2006.01)
(52) U.S. Cl.
USPC ............................... 424/94.6; 514/19.3
(58) Field of Classification Search
USPC ........................................ 424/94.6; 514/19.3
See application file for complete search history.

(56) References Cited

U.S. PATENT DOCUMENTS

| | | | | |
|---|---|---|---|---|
| 2005/0244398 | A1 | 11/2005 | Cheng et al. | 424/94.4 |
| 2008/0226617 | A1 | 9/2008 | Cheng et al. | 424/94.6 |
| 2008/0292609 | A1* | 11/2008 | Cheng et al. | 424/94.6 |
| 2009/0238813 | A1* | 9/2009 | Georgiou et al. | 424/94.6 |
| 2010/0247508 | A1* | 9/2010 | Leung et al. | 424/94.6 |

FOREIGN PATENT DOCUMENTS

| | | |
|---|---|---|
| WO | WO 03/063780 | 8/2003 |
| WO | WO 04/001048 | 12/2003 |

OTHER PUBLICATIONS

Kang J. et al. Emerging PEGylated Drugs Expert Opinion Emerging Drugs 14(2)363-380, Jun. 2009.*
Stone E. et al. Strategies for Optimizing the Serum Persistence of Engineered Human Arginase I for Cancer Therapy. J of Controlled Release 158(1)171-179, Oct. 2011.*
Cellarier et al., "Methionine dependency and cancer treatment," *Cancer Treat. Rev.*, 29:489-499, 2003.
Cheng et al., "Enhanced hepatocyte growth factor signaling by type II transforming growth factor-beta receptor knockout fibroblasts promotes mammary tumorigenesis," *Cancer Res.*, 67:4869-4877, 2007.
Cheng et al., "Pegylated recombinant human arginase (rhArg-pegs$_{5,000mw}$) inhibits the in vitro and in vivo proliferation of human hepatocellular carcinoma through arginine depletion," *Cancer Res.*, 67(1):309-317, 2007.
Cheng et al., "Remission of hepatocellular carcinoma with arginine depletion induced by systemic release of endogenous hepatic arginase due to transhepatic arterial embolisation, augmented by high-dose insulin: arginase as a potential drug candidate for hepatocellular carcinoma," *Cancer Lett.*, 224:67-80, 2005.
Dillon et al., "Biochemical characterization of the arginine degrading enzymes arginase and arginine deiminase and their effect on nitric oxide production," *Med. Sci. Monit.*, 8:BR248-253, 2002.
Dinndorf et al., "FDA drug approval summary: pegaspargase (oncaspar) for the first-line treatment of children with acute lymphoblastic leukemia (ALL)," *Oncologist*, 12:991-998, 2007.
Ensor et al., "Pegylated arginine deiminase (ADI-SS PEG$_{20,000\ mw}$) inhibits human melanomas and hepatocellular carcinomas in vitro and in vivo," *Cancer Res.*, 62:5443-5450, 2002.
Feun et al., "Clinical trial of CPT-11 and VM-26/VP-16 for patients with recurrent malignant brain tumors," *J. Neurooncol.*, 82:177-181, 2007.
Holtsberg et al., "Poly(ethylene glycol) (PEG) conjugated arginine deiminase: effects of PEG formulations on its pharmacological properties," *Journal of Controlled Release*, 80:259-271, 2002.
Ikemoto et al., "Expression of human liver arginase in *Escherichia coli*: purification and properties of the product," *Biochem. J.*, 270:697-703, 1990.
Jenkinson et al., "Comparative properties of arginases," *Comp. Biochem. Physiol.*, 114B(1):107-132, 1996.
Lamb and Wheatley, "Single Amino Acid (Arginine) Deprivation Induces G1 Arrest Associated with Inhibition of Cdk4 Expression in Cultured Human Diploid Fibroblasts," *Experimental Cell Res.*, 255:238-249, 2000.
Lavulo et al., "Subunit-subunit interactions in trimeric arginase: generation of active monomers by mutation of a single amino acid," *The Journal of Biological Chemistry*, 276(17):14242-14248, 2001.
López et al., "Insights into the interaction of human arginase II with substrate and manganese ions by site-directed mutagenesis and kinetic studies. Alteration of substrate specificity by replacement of Asn149 with Asp," *Febs J.*, 272:4540-4548, 2005.
Malumbres & Barbacid, "To cycle or not to cycle: a critical decision in cancer," *Nature Rev. Cancer*, 1:222-231, 2001.
PCT International Preliminary Report on Patentability issued in International Application No. PCT/US2010/040205, mailed Jan. 12, 2012.
PCT International Search Report and Written Opinion issued in International Application No. PCT/US2010/040205, mailed Mar. 25, 2011.

(Continued)

*Primary Examiner* — Ralph Gitomer
(74) *Attorney, Agent, or Firm* — Parker Highlander PLLC

(57) ABSTRACT

Methods and composition for generation of arginase variants with high serum persistence are provided. For example, in certain aspects methods for purifying pegylated arginase are described. Furthermore, the invention provides stabilized arginase multimers or pharmaceutical composition thereof.

9 Claims, 3 Drawing Sheets

(56) References Cited

OTHER PUBLICATIONS

Savoca et al., "Cancer therapy with chemically modified enzymes. II. The therapeutic effectiveness of arginase, and arginase modified by the covalent attachment of polyethylene glycol, on the taper liver tumor and the L5178Y murine leukemia," *Cancer Biochem. Biophys.*, 7:261-268, 1984.

Scott et al., "Single amino acid (arginine) deprivation: rapid and selective death of cultured transformed and malignant cells," *Br. J. Cancer*, 83:800-810, 2000.

Seely et al., "Making site-specific PEGylation work," *BioPharm International*, 2005.

Shen et al., "Modulation of arginine metabolic pathways as the potential anti-tumor mechanism of recombinant arginine deiminase," *Cancer Lett.*, 231:30-35, 2006.

Storr & Burton, "The effects of arginine deficiency on lymphoma cells," *Br. J. Cancer*, 30:50-59, 1974.

Tsui et aL, "Pegylated derivatives of recombinant human arginase (rhArgI) for sustained in vivo activity in cancer therapy: preparation, characterization and analysis of their pharmacodynamics in vivo and in vitro and action upon hepatocellular carcinoma cell (HCC)," *Cancer Cell International*, 9:9, 2009.

Wetzler et al., "Effective asparagine depletion with pegylated asparaginase results in improved outcomes in adult acute lymphoblastic leukemia: Cancer and Leukemia Group B Study 9511," *Blood*, 109:4164-4167, 2007.

Wheatley and Campbell, "Arginine catabolism, liver extracts and cancer," *Pathol. Oncol. Res.*, 8:18-25, 2002.

Wheatley at al., "Single amino acid (arginine) restriction: growth and death of cultured HeLa and human diploid fibroblasts," *Cellular Physiol. Biochem.*, 10:37-55, 2000.

Yoon et al., "Renal cell carcinoma does not express argininosuccinate synthetase and is highly sensitive to arginine deprivation via arginine deiminase," *Int. J. Cancer*, 120:897-905, 2007.

* cited by examiner

SEQUENCE LISTING

<160> NUMBER OF SEQ ID NOS: 6

<210> SEQ ID NO 1
<211> LENGTH: 334
<212> TYPE: PRT
<213> ORGANISM: Homo sapiens

<400> SEQUENCE: 1

| Met | Gly | Cys | Ser | His | His | His | His | His | Ser | Ser | Gly | Ser | Ala | Lys |
| 1   |     |     |     | 5   |     |     |     |     | 10  |     |     |     |     | 15  |

| Ser | Arg | Thr | Ile | Gly | Ile | Ile | Gly | Ala | Pro | Phe | Ser | Lys | Gly | Gln | Pro |
|     |     |     | 20  |     |     |     |     | 25  |     |     |     |     | 30  |     |     |

| Arg | Gly | Gly | Val | Glu | Glu | Gly | Pro | Thr | Val | Leu | Arg | Lys | Ala | Gly | Leu |
|     |     | 35  |     |     |     |     | 40  |     |     |     |     | 45  |     |     |     |

| Leu | Glu | Lys | Leu | Lys | Gln | Glu | Cys | Asp | Val | Lys | Asp | Tyr | Gly | Asp |
|     | 50  |     |     |     |     | 55  |     |     |     |     | 60  |     |     |     |

| Leu | Pro | Phe | Ala | Asp | Ile | Pro | Asn | Asp | Ser | Pro | Phe | Gln | Ile | Val | Lys |
| 65  |     |     |     |     | 70  |     |     |     |     | 75  |     |     |     |     | 80  |

| Asn | Pro | Arg | Ser | Val | Gly | Lys | Ala | Ser | Glu | Gln | Leu | Ala | Gly | Lys | Val |
|     |     |     |     | 85  |     |     |     |     | 90  |     |     |     |     | 95  |     |

| Ala | Glu | Val | Lys | Lys | Asn | Gly | Arg | Ile | Ser | Leu | Val | Leu | Gly | Gly | Asp |
|     |     |     | 100 |     |     |     |     | 105 |     |     |     |     | 110 |     |     |

| His | Ser | Leu | Ala | Ile | Gly | Ser | Ile | Ser | Gly | His | Ala | Arg | Val | His | Pro |
|     |     | 115 |     |     |     |     | 120 |     |     |     |     | 125 |     |     |     |

| Asp | Leu | Gly | Val | Ile | Trp | Val | Asp | Ala | His | Thr | Asp | Ile | Asn | Thr | Pro |
|     | 130 |     |     |     |     | 135 |     |     |     |     | 140 |     |     |     |     |

| Leu | Thr | Thr | Thr | Ser | Gly | Asn | Leu | His | Gly | Gln | Pro | Val | Ser | Phe | Leu |
| 145 |     |     |     |     | 150 |     |     |     |     | 155 |     |     |     |     | 160 |

| Leu | Lys | Glu | Leu | Lys | Gly | Lys | Ile | Pro | Asp | Val | Pro | Gly | Phe | Ser | Trp |
|     |     |     |     | 165 |     |     |     |     | 170 |     |     |     |     | 175 |     |

| Val | Thr | Pro | Cys | Ile | Ser | Ala | Lys | Asp | Ile | Val | Tyr | Ile | Gly | Leu | Arg |
|     |     |     | 180 |     |     |     |     | 185 |     |     |     |     | 190 |     |     |

| Asp | Val | Asp | Pro | Gly | Glu | His | Tyr | Ile | Leu | Lys | Thr | Leu | Gly | Ile | Lys |
|     | 195 |     |     |     |     | 200 |     |     |     |     | 205 |     |     |     |     |

| Tyr | Phe | Ser | Met | Thr | Glu | Val | Asp | Arg | Leu | Gly | Ile | Gly | Lys | Val | Met |
|     | 210 |     |     |     |     | 215 |     |     |     |     | 220 |     |     |     |     |

| Glu | Glu | Thr | Leu | Ser | Tyr | Leu | Leu | Gly | Arg | Lys | Lys | Arg | Pro | Ile | His |
| 225 |     |     |     |     | 230 |     |     |     |     | 235 |     |     |     |     | 240 |

| Leu | Ser | Phe | Asp | Val | Asp | Gly | Leu | Asp | Pro | Ser | Phe | Thr | Pro | Ala | Thr |
|     |     |     |     | 245 |     |     |     |     | 250 |     |     |     |     | 255 |     |

| Gly | Thr | Pro | Val | Val | Gly | Gly | Leu | Thr | Tyr | Arg | Glu | Gly | Leu | Tyr | Ile |
|     |     |     | 260 |     |     |     |     | 265 |     |     |     |     | 270 |     |     |

| Thr | Glu | Glu | Ile | Tyr | Lys | Thr | Gly | Leu | Leu | Ser | Gly | Leu | Asp | Ile | Met |
|     |     | 275 |     |     |     |     | 280 |     |     |     |     | 285 |     |     |     |

| Glu | Val | Asn | Pro | Ser | Leu | Gly | Lys | Thr | Pro | Glu | Glu | Val | Thr | Arg | Thr |
|     | 290 |     |     |     |     | 295 |     |     |     |     | 300 |     |     |     |     |

| Val | Asn | Thr | Ala | Val | Ala | Ile | Thr | Leu | Ala | Cys | Phe | Gly | Leu | Ala | Arg |
| 305 |     |     |     |     | 310 |     |     |     |     | 315 |     |     |     |     | 320 |

| Glu | Gly | Asn | His | Lys | Pro | Ile | Asp | Tyr | Leu | Asn | Pro | Pro | Lys |
|     |     |     |     | 325 |     |     |     |     | 330 |     |     |     |     |

<210> SEQ ID NO 2
<211> LENGTH: 1005
<212> TYPE: DNA
<213> ORGANISM: Homo sapiens

<400> SEQUENCE: 2

```
atgggttgtt ctcaccatca tcaccaccac agctctggct ctgcgaagag ccgtacgatc      60
ggcattattg gtgcgccgtt ctctaaaggt cagccacgcg gtggtgtgga agagggtccg     120
acggttctgc gtaaggccgg tttattagaa aagctgaaag agcaggagtg cgacgttaag     180
gactacggtg acttaccatt cgcggacatc ccgaatgata gcccgttcca aatcgttaag     240
```

```
aatccgcgct ctgtgggtaa agcaagcgag cagttagcag gtaaggtggc cgaggtcaag    300
aaaaacggtc gtattagcct ggttttaggc ggtgatcata gcttagcaat tggctctatc    360
tctggtcatg cccgtgtgca cccagattta ggtgtcattt gggttgacgc ccatacggat    420
atcaatacgc cattaacgac caccagcggc aatctgcatg ccagccggt tagcttctta     480
ctgaaggagc tgaagggtaa aattccagat gttccgggct ttagctgggt cacgccatgt    540
atttctgcca aggatatcgt gtacattggc ttacgtgacg tcgacccagg tgagcactac    600
atcttaaaga ccctgggtat caagtatttc agcatgacgg aagtggaccg cttaggcatc    660
ggcaaggtga tggaggagac gctgagctat ctgctgggcc gtaagaaacg tccaatccat    720
ctgagcttcg atgttgacgg cttagacccg agctttacgc cagccaccgg cacgccggtc    780
gttggtggtt taacgtatcg cgaaggcctg tatatcacgg aggaaatcta aagacgggt     840
ttactgagcg gtctggacat tatggaggtt aatccaagct taggtaagac gccggaagaa    900
gttacccgta ccgttaacac ggcggtcgcg atcacgttag catgtttcgg tttagcccgc    960
gagggcaacc ataaaccaat tgattatctg aatccaccga agtga                    1005

<210> SEQ ID NO 3
<211> LENGTH: 1030
<212> TYPE: PRT
<213> ORGANISM: Homo sapiens

<400> SEQUENCE: 3

Met Gly Ser Ser His His His His His His Ser Ser Gly Glu Asn Leu
1               5                   10                  15

Tyr Phe Gln Ser Ala Lys Ser Arg Thr Ile Gly Ile Ile Gly Ala Pro
                20                  25                  30

Phe Ser Lys Gly Gln Pro Arg Gly Gly Val Glu Glu Gly Pro Thr Val
            35                  40                  45

Leu Arg Lys Ala Gly Leu Leu Glu Lys Leu Lys Glu Gln Glu Cys Asp
        50                  55                  60

Val Lys Asp Tyr Gly Asp Leu Pro Phe Ala Asp Ile Pro Asn Asp Ser
65                  70                  75                  80

Pro Phe Gln Ile Val Lys Asn Pro Arg Ser Val Gly Lys Ala Ser Glu
                85                  90                  95

Gln Leu Ala Gly Lys Val Ala Glu Val Lys Lys Asn Gly Arg Ile Ser
            100                 105                 110

Leu Val Leu Gly Gly Asp His Ser Leu Ala Ile Gly Ser Ile Ser Gly
        115                 120                 125

His Ala Arg Val His Pro Asp Leu Gly Val Ile Trp Val Asp Ala His
    130                 135                 140

Thr Asp Ile Asn Thr Pro Leu Thr Thr Ser Gly Asn Leu His Gly
145                 150                 155                 160

Gln Pro Val Ser Phe Leu Leu Lys Glu Leu Lys Gly Lys Ile Pro Asp
                165                 170                 175

Val Pro Gly Phe Ser Trp Val Thr Pro Cys Ile Ser Ala Lys Asp Ile
            180                 185                 190

Val Tyr Ile Gly Leu Arg Asp Val Asp Pro Gly Glu His Tyr Ile Leu
        195                 200                 205

Lys Thr Leu Gly Ile Lys Tyr Phe Ser Met Thr Glu Val Asp Arg Leu
    210                 215                 220

Gly Ile Gly Lys Val Met Glu Glu Thr Leu Ser Tyr Leu Leu Gly Arg
225                 230                 235                 240

Lys Lys Arg Pro Ile His Leu Ser Phe Asp Val Asp Gly Leu Asp Pro
```

-continued

```
                245                 250                 255
Ser Phe Thr Pro Ala Thr Gly Thr Pro Val Val Gly Gly Leu Thr Tyr
            260                 265                 270

Arg Glu Gly Leu Tyr Ile Thr Glu Glu Ile Tyr Lys Thr Gly Leu Leu
        275                 280                 285

Ser Gly Leu Asp Ile Met Glu Val Asn Pro Ser Leu Gly Lys Thr Pro
    290                 295                 300

Glu Glu Val Thr Arg Thr Val Asn Thr Ala Val Ala Ile Thr Leu Ala
305                 310                 315                 320

Cys Phe Gly Leu Ala Arg Glu Gly Asn His Lys Pro Ile Asp Tyr Leu
                325                 330                 335

Asn Pro Pro Lys Gly Ser Gly Ser Gly Ser Gly Ser Gly Ser Gly Ser
            340                 345                 350

Gly Ser Gly Ser Gly Ser Gly Ser Gly Glu Phe Ser Ala Lys Ser Arg
        355                 360                 365

Thr Ile Gly Ile Ile Gly Ala Pro Phe Ser Lys Gly Gln Pro Arg Gly
    370                 375                 380

Gly Val Glu Glu Gly Pro Thr Val Leu Arg Lys Ala Gly Leu Leu Glu
385                 390                 395                 400

Lys Leu Lys Glu Gln Glu Cys Asp Val Lys Asp Tyr Gly Asp Leu Pro
                405                 410                 415

Phe Ala Asp Ile Pro Asn Asp Ser Pro Phe Gln Ile Val Lys Asn Pro
            420                 425                 430

Arg Ser Val Gly Lys Ala Ser Glu Gln Leu Ala Gly Lys Val Ala Glu
        435                 440                 445

Val Lys Lys Asn Gly Arg Ile Ser Leu Val Leu Gly Gly Asp His Ser
    450                 455                 460

Leu Ala Ile Gly Ser Ile Ser Gly His Ala Arg Val His Pro Asp Leu
465                 470                 475                 480

Gly Val Ile Trp Val Asp Ala His Thr Asp Ile Asn Thr Pro Leu Thr
                485                 490                 495

Thr Thr Ser Gly Asn Leu His Gly Gln Pro Val Ser Phe Leu Leu Lys
            500                 505                 510

Glu Leu Lys Gly Lys Ile Pro Asp Val Pro Gly Phe Ser Trp Val Thr
        515                 520                 525

Pro Cys Ile Ser Ala Lys Asp Ile Val Tyr Ile Gly Leu Arg Asp Val
    530                 535                 540

Asp Pro Gly Glu His Tyr Ile Leu Lys Thr Leu Gly Ile Lys Tyr Phe
545                 550                 555                 560

Ser Met Thr Glu Val Asp Arg Leu Gly Ile Gly Lys Val Met Glu Glu
                565                 570                 575

Thr Leu Ser Tyr Leu Leu Gly Arg Lys Lys Arg Pro Ile His Leu Ser
            580                 585                 590

Phe Asp Val Asp Gly Leu Asp Pro Ser Phe Thr Pro Ala Thr Gly Thr
        595                 600                 605

Pro Val Val Gly Gly Leu Thr Tyr Arg Glu Gly Leu Tyr Ile Thr Glu
    610                 615                 620

Glu Ile Tyr Lys Thr Gly Leu Leu Ser Gly Leu Asp Ile Met Glu Val
625                 630                 635                 640

Asn Pro Ser Leu Gly Lys Thr Pro Glu Glu Val Thr Arg Thr Val Asn
                645                 650                 655

Thr Ala Val Ala Ile Thr Leu Ala Cys Phe Gly Leu Ala Arg Glu Gly
            660                 665                 670
```

Asn His Lys Pro Ile Asp Tyr Leu Asn Pro Pro Lys Gly Gly Ser Ser
            675                 680                 685

Gly Gly Ser Ser Gly Gly Ser Ser Gly Gly Ser Ser Gly Gly Ser Ser
        690                 695                 700

Gly Gly Ala Ala Ala Ser Ala Lys Ser Arg Thr Ile Gly Ile Ile Gly
705                 710                 715                 720

Ala Pro Phe Ser Lys Gly Gln Pro Arg Gly Val Glu Glu Gly Pro
            725                 730                 735

Thr Val Leu Arg Lys Ala Gly Leu Leu Glu Lys Leu Lys Glu Gln Glu
            740                 745                 750

Cys Asp Val Lys Asp Tyr Gly Asp Leu Pro Phe Ala Asp Ile Pro Asn
            755                 760                 765

Asp Ser Pro Phe Gln Ile Val Lys Asn Pro Arg Ser Val Gly Lys Ala
            770                 775                 780

Ser Glu Gln Leu Ala Gly Lys Val Ala Glu Val Lys Lys Asn Gly Arg
785                 790                 795                 800

Ile Ser Leu Val Leu Gly Gly Asp His Ser Leu Ala Ile Gly Ser Ile
                805                 810                 815

Ser Gly His Ala Arg Val His Pro Asp Leu Gly Val Ile Trp Val Asp
            820                 825                 830

Ala His Thr Asp Ile Asn Thr Pro Leu Thr Thr Thr Ser Gly Asn Leu
            835                 840                 845

His Gly Gln Pro Val Ser Phe Leu Leu Lys Glu Leu Lys Gly Lys Ile
            850                 855                 860

Pro Asp Val Pro Gly Phe Ser Trp Val Thr Pro Cys Ile Ser Ala Lys
865                 870                 875                 880

Asp Ile Val Tyr Ile Gly Leu Arg Asp Val Asp Pro Gly Glu His Tyr
                885                 890                 895

Ile Leu Lys Thr Leu Gly Ile Lys Tyr Phe Ser Met Thr Glu Val Asp
                900                 905                 910

Arg Leu Gly Ile Gly Lys Val Met Glu Glu Thr Leu Ser Tyr Leu Leu
            915                 920                 925

Gly Arg Lys Lys Arg Pro Ile His Leu Ser Phe Asp Val Asp Gly Leu
            930                 935                 940

Asp Pro Ser Phe Thr Pro Ala Thr Gly Thr Pro Val Val Gly Gly Leu
945                 950                 955                 960

Thr Tyr Arg Glu Gly Leu Tyr Ile Thr Glu Glu Ile Tyr Lys Thr Gly
                965                 970                 975

Leu Leu Ser Gly Leu Asp Ile Met Glu Val Asn Pro Ser Leu Gly Lys
            980                 985                 990

Thr Pro Glu Glu Val Thr Arg Thr Val Asn Thr Ala Val Ala Ile Thr
            995                 1000                1005

Leu Ala Cys Phe Gly Leu Ala Arg Glu Gly Asn His Lys Pro Ile
    1010                1015                1020

Asp Tyr Leu Asn Pro Pro Lys
    1025                1030

<210> SEQ ID NO 4
<211> LENGTH: 3093
<212> TYPE: DNA
<213> ORGANISM: Homo sapiens

<400> SEQUENCE: 4
atgggttctt ctcaccatca tcaccaccac agctctggcg agaacctgta cttccagtct      60
gcgaagagcc gtacgatcgg cattattggt gcgccgttct ctaaaggtca gccacgcggt     120

```
ggtgtggaag agggtccgac ggttctgcgt aaggccggtt tattagaaaa gctgaaagag    180
caggagtgcg acgttaagga ctacggtgac ttaccattcg cggacatccc gaatgatagc    240
ccgttccaaa tcgttaagaa tccgcgctct gtgggtaaag caagcgagca gttagcaggt    300
aaggtggccg aggtcaagaa aaacggtcgt attagcctgg ttttaggcgg tgatcatagc    360
ttagcaattg gctctatctc tggtcatgcc cgtgtgcacc cagatttagg tgtcatttgg    420
gttgacgccc atacggatat caatacgcca ttaacgacca ccagcggcaa tctgcatggc    480
cagccggtta gcttcttact gaaggagctg aagggtaaaa ttccagatgt tccgggcttt    540
agctgggtca cgccatgtat ttctgccaag gatatcgtgt acattggctt acgtgacgtc    600
gacccaggtg agcactacat cttaaagacc ctgggtatca gtatttcag catgacggaa     660 gtggaccgct taggcatcgg caaggtgatg gaggagacgc tgagctatct gctgggccgt    720
aagaaacgtc caatccatct gagcttcgat gttgacggct tagacccgag ctttacgcca    780
gccaccggca cgccggtcgt tggtggttta acgtatcgcg aaggcctgta tatcacggag    840
gaaatctata gacgggttt actgagcggt ctggacatta tggaggttaa tccaagctta    900
ggtaagacgc cggaagaagt tacccgtacc gttaacacgg cggtcgcgat cacgttagca    960
tgtttcggtt tagcccgcga gggcaaccat aaaccaattg attatctgaa tccaccgaag   1020
ggcagcggca gcggctctgg ttctggtagc ggttctggct ctggcagcgg cagcggctct   1080
ggtgaattct ctgcgaagag ccgtacgatc ggcattattg gtgcgccgtt ctctaaaggt   1140
cagccacgcg gtggtgtgga agagggtccg acggttctgc gtaaggccgg tttattagaa   1200
aagctgaaag agcaggagtg cgacgttaag gactacggtg acttaccatt cgcggacatc   1260
ccgaatgata gcccgttcca aatcgttaag aatccgcgct ctgtgggtaa agcaagcgag   1320
cagttagcag gtaaggtggc cgaggtcaag aaaaacggtc gtattagcct ggttttaggc   1380
ggtgatcata gcttagcaat tggctctatc tctggtcatg cccgtgtgca cccagattta   1440
ggtgtcattt gggttgacgc ccatacggat atcaatacgc cattaacgac caccagcggc   1500
aatctgcatg ccagccggt tagcttctta ctgaaggagc tgaagggtaa aattccagat   1560
gttccgggct ttagctgggt cacgccatgt atttctgcca aggatatcgt gtacattggc   1620
ttacgtgacg tcgacccagg tgagcactac atcttaaaga ccctgggtat caagtatttc   1680
agcatgacgg aagtggaccg cttaggcatc ggcaaggtga tggaggagac gctgagctat   1740
ctgctgggcc gtaagaaacg tccaatccat ctgagcttcg atgttgacgg cttagacccg   1800
agctttacgc cagccaccgg cacgccggtc gttggtggtt taacgtatcg cgaaggcctg   1860
tatatcacgg aggaaatcta taagacgggt ttactgagcg gtctggacat tatggaggtt   1920
aatccaagct taggtaagac gccggaagaa gttacccgta ccgttaacac ggcggtcgcg   1980
atcacgttag catgtttcgg tttagcccgc gagggcaacc ataaaccaat tgattatctg   2040
aatccaccga agggcggcag ctctggcggt tcttctggtg gtagcagcgg cggtagctct   2100
ggcggctcta gcgtggtgc ggccgcatct gcgaagagcc gtacgatcgg cattattggt   2160
gcgccgttct ctaaaggtca gccacgcggt ggtgtggaag agggtccgac ggttctgcgt   2220
aaggccggtt tattagaaaa gctgaaagag caggagtgcg acgttaagga ctacggtgac   2280
ttaccattcg cggacatccc gaatgatagc ccgttccaaa tcgttaagaa tccgcgctct   2340
gtgggtaaag caagcgagca gttagcaggt aaggtggccg aggtcaagaa aaacggtcgt   2400
attagcctgg ttttaggcgg tgatcatagc ttagcaattg gctctatctc tggtcatgcc   2460
cgtgtgcacc cagatttagg tgtcatttgg gttgacgccc atacggatat caatacgcca   2520
```

```
ttaacgacca ccagcggcaa tctgcatggc cagccggtta gcttcttact gaaggagctg    2580
aagggtaaaa ttccagatgt tccgggcttt agctgggtca cgccatgtat ttctgccaag    2640
gatatcgtgt acattggctt acgtgacgtc gacccaggtg agcactacat cttaaagacc    2700
ctgggtatca agtatttcag catgacggaa gtggaccgct taggcatcgg caaggtgatg    2760
gaggagacgc tgagctatct gctgggccgt aagaaacgtc caatccatct gagcttcgat    2820
gttgacggct tagacccgag ctttacgcca gccaccggca cgccggtcgt tggtggttta    2880
acgtatcgcg aaggcctgta tcacggag gaaatctata agacgggttt actgagcggt    2940
ctggacatta tggaggttaa tccaagctta ggtaagacgc cggaagaagt tacccgtacc    3000
gttaacacgg cggtcgcgat cacgttagca tgtttcggtt tagcccgcga gggcaaccat    3060
aaaccaattg attatctgaa tccaccgaag tga                                 3093
```

```
<210> SEQ ID NO 5
<211> LENGTH: 20
<212> TYPE: PRT
<213> ORGANISM: Artificial Sequence
<220> FEATURE:
<223> OTHER INFORMATION: Synthetic peptide

<400> SEQUENCE: 5

Gly Ser Gly Ser Gly Ser Gly Ser Gly Ser Gly Ser Gly Ser Gly Ser
1               5                   10                  15

Gly Ser Gly Ser
            20

<210> SEQ ID NO 6
<211> LENGTH: 20
<212> TYPE: PRT
<213> ORGANISM: Artificial Sequence
<220> FEATURE:
<223> OTHER INFORMATION: Synthetic peptide

<400> SEQUENCE: 6

Gly Gly Ser Ser Gly Gly Ser Ser Gly Gly Ser Ser Gly Gly Ser Ser
1               5                   10                  15

Gly Gly Ser Ser
            20
```

METHODS FOR PURIFYING PEGYLATED ARGINASE

The present application is a national phase application under 35 U.S.C. §371 of International Application No. PCT/US2010/040205 filed Jun. 28, 2010 which claims the priority benefit of U.S. Provisional Application Ser. No. 61/221,396, filed Jun. 29, 2009 the entire contents of which are incorporated herein by reference.

The sequence listing that is contained in the file "GGEOP0003US_ST25.txt", which is 18 KB (as measured in Microsoft Windows®) and was created on Jan. 23, 2014, is filed herewith by electronic submission and is incorporated by reference herein.

BACKGROUND OF THE INVENTION

1. Field of the Invention

The present invention relates generally to the field of protein therapeutics. More particularly, it concerns improved methods and compositions for producing human arginases modified for long stability and persistence in humans.

2. Description of Related Art

It has been recognized for over 50 years that certain tumor cells have a high demand for L-Arginine and are killed under conditions of L-Arginine depletion (Wheatley and Campbell, 2002). In human cells L-Arginine is synthesized in two steps: first argininosuccinate synthetase (ASS) converts L-Citrulline and L-Aspartate to argininosuccinate, followed by conversion of argininosuccinate to L-Arginine and fumarate by argininosuccinate lyase. L-Citrulline itself is synthesized from L-Ornithine and carbamoyl phosphate by the enzyme ornithine transcarbamylase (OTC). A large number of hepatocellular carcinomas, melanomas, and, as discovered recently, renal cell carcinomas (Ensor et al., 2002; Feun et al., 2007; Yoon et al., 2007) do not express ASS and thus are sensitive to L-Arginine depletion. The molecular basis for the lack of ASS expression appears to be diverse and includes aberrant gene regulation and splicing defects. Whereas non-malignant cells enter into quiescence ($G_0$) when depleted of L-Arginine and thus remain viable for several weeks, tumor cells have cell cycle defects that lead to the re-initiation of DNA synthesis even though protein synthesis is inhibited, in turn resulting in major imbalances and rapid cell death (Shen et al., 2006; Scott et al., 2000). The selective toxicity of L-Arginine depletion for HCC, melanoma and other ASS-deficient cancer cells has been extensively demonstrated in vitro, in xenograft animal models and in clinical trials I Shen et al., 2006; Ensor et al., 2002; Feun et al., 2007; Izzo et al., 2004). Recently Cheng et al. (2007) demonstrated that many HCC cells are also deficient in ornithine transcarbamylase expression and thus, they are also susceptible to enzymatic L-Arginine depletion.

There is interest in the use of L-Arginine hydrolytic enzymes for cancer therapy. Two L-Arginine degrading enzymes have been studied for cancer therapy: bacterial arginine deiminase and human Arginase. Unfortunately, both of these enzymes display significant shortcomings that present major impediments to clinical use (immunogenicity and low catalytic activity in serum, respectively). Thus, there is a need to develop improved compositions and methods for L-Arginine depletion cancer therapy, especially to develop therapeutics for L-Arginine depletion therapy that display favorable pharmacokinetics in humans including long persistence in circulation

SUMMARY OF THE INVENTION

The present invention overcomes a major deficiency in the art by providing methods and compositions for preparing arginase variants with increased circulation persistence, which are more suitable for cancer therapy. In a first embodiment, the invention involves a stabilized multimeric arginase comprising at least two arginase monomers conjugated to form the stabilized arginase, which may be further defined as stabilized human arginase, such as stabilized human arginase I or human arginase II. In a further embodiment, the stabilized arginase may comprise cobalt as its metal cofactor to further improve the rate of hydrolysis of L-Arginine and the stability of the enzyme in serum. Preferably, the stabilized arginase may be further defined as a fusion protein wherein at least two arginase monomers are fused as a linear polypeptide comprising one or more flexible linkers positioned between one or more monomers, such as $[(Gly)_4\text{-Ser}]_n$ (n=the number of repeats) linkers or any other peptide linkers known in the art. One example of the fusion protein sequence may be set forth in SEQ ID NO:3, as encoded by SEQ ID NO:4. Alternatively, the monomers may be chemically conjugated to form such a stabilized multimeric arginase. The stabilized arginase may comprise two to four arginase monomers to achieve high molecular weight above the cut-off for renal filtration, and a stabilized trimeric form may be an example.

The invention also discloses an arginase formulation that displays a long half-life and a high degree of homogeneity, for example, an arginase formulation comprising a human arginase pegylated an engineered Cys residue at the C- or N-terminus. Conjugation of proteins to polyethylene glycol (PEG) or pegylation is widely employed in the art to increase the molecular weight of protein therapeutics and thus increase retention in circulation by preventing filtration through the kidneys. Protein pegylation involves the chemical conjugation of PEG molecules of appropriate size to one or more reactive groups in a protein, typically —NH, COOH, —OH, or —SH groups. Proteins typically contain multiple —NH, —COOH or —OH reactive groups and therefore chemical conjugation of PEG results in the production of a heterogeneous protein sample consisting of polypeptides containing one or multiple PEG chains attached to various reactive groups. Such heterogeneously PEGylated proteins display complex pharmacological properties and stability and therefore are generally undesirable for therapeutic purposes. However many proteins do not contain any —SH reactive groups. In those cases it is possible to engineer the protein to introduce an exposed Cys residue, typically at the C- or N-terminus. The engineered Cys amino acid endows the protein with a single reactive —SH group. The single —SH can then be reacted with —SH specific PEG moiety resulting in the formation of a chemically homogenous protein-PEG conjugate. The process whereby a protein is modified by reaction with a single PEG molecule at a specified aa is called site specific PEGylation. Human Arginase I contains three Cys residues which however are partially or completely buried within the three dimensional structure of the native protein.

The inventors found that the three native Cys in human Arginase are relatively inaccessible to modification with —SH-reactive PEG molecules. The inventors further found that modification of one or more of the three native Cys aa in human arginase is slow, and results in the deactivation of the enzyme. The inventors also found that if an engineered, accessible Cys is introduced at the terminus of the protein then that Cys can readily react with —SH reactive PEG polymer without loss of activity. Additionally the inventors have found that when engineered human arginase containing a terminal Cys is reacted with an excess of —SH reactive PEG molecules for long times the extent of reaction is increased to near 100% but under these conditions the buried native Cys residues in the protein also become modified and thus the protein is mostly inactivated. The inventors realized that the reaction of engineered human arginase containing a terminal Cys with a low stoichiometric excess of —SH specific PEG for a short time prevents the inactivation of the protein. However under those conditions the extent of reaction, i.e., the extent of PEGylated Cys-containing human arginase is less than 100% and typically between 40-70%.

Human arginase I is a trimer comprising of three identical polypeptides which undergoes trimer-monomer equilibrium in vivo. PEG conjugation under conditions that result in full retention of the enzymatic activity lead to the formation of a mixture of human arginase trimers comprising of trimers in which every monomer polypeptide has been reacted with PEG and also trimers in which two or only one monomer polypeptide has been reacted with PEG. The trimers in which all three polypeptides have been conjugated to PEG are desirable for therapeutic purposes. Trimers containing one or more unpegylated polypeptides may be prone to filtration in the kidneys and display a short half-life. The desired trimers whereby each of the constituent monomers is conjugated to PEG cannot be separated from trimers containing only one or two PEGylated monomers by standard biochemical techniques such as gel filtration chromatography in physiological buffers. However, the inventors discovered that temporary incubation of human arginase conjugated to —SH reactive PEG at a pH lower than the physiological pH dramatically facilitates isolation of trimeric human arginase in which every polypeptide is conjugated to a single PEG chain (i.e., a trimer with three PEG chains) from other forms containing one or two PEG moieties.

Thus, certain further embodiments of the present invention provide a method for separating pegylated arginase from unpegylated arginase, comprising: a) obtaining a protein solution comprising pegylated arginase and unpegylated arginase; and b) separating the pegylated arginase from the unpegylated arginase at a pH from about 3 to about 5.5, preferably, about 3.5 to about 5.0, more preferably, about 4.5, or any intervening range or values. For potential application in human cancer therapy, the pegylated arginase may be further defined as pegylated human arginase, such as pegylated human arginase I or pegylated human arginase II. Preferably, the pegylated arginase may be pegylated at an engineered cysteine residue, for example, a N-terminal cysteine substitution of the arginase, as exemplified by SEQ ID NO:1, which is encoded by SEQ ID NO:2. To further increase the kinetics and serum persistence, the pegylated arginase may comprise cobalt as its metal cofactor. In a certain aspect, the pegylated arginase may be separated from the unpegylated arginase by size exclusion chromatography or any purification methods based on the size.

The inventors have found that unmodified human Arginase is very susceptible to filtration in the kidneys and thus following IV (intravenous) administration in a mammal it is lost from circulation with a half life of less than one hour. The inventors then developed novel arginase variants with improved pharmacokinetics for potential cancer treatments. In still further embodiments of the invention a stabilized multimeric arginase comprising at least two arginase monomers conjugated to form the stabilized arginase with long half-life, wherein the stabilized arginase has a serum half-life, especially following IV injection in a mammal, of about 5 hours to 100 hours, about 10 hours to 100 hours, about 7 to 35 hours, or any range or value derivable therein.

Embodiments discussed in the context of methods and/or compositions of the invention may be employed with respect to any other method or composition described herein. Thus, an embodiment pertaining to one method or composition may be applied to other methods and compositions of the invention as well.

As used herein the terms "encode" or "encoding" with reference to a nucleic acid are used to make the invention readily understandable by the skilled artisan; however, these terms may be used interchangeably with "comprise" or "comprising" respectively.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 2A. Fractions of hArgI conjugated with Peg20K, separated by SEC in a sodium acetate buffer at pH 4.5. FIG. 2B. Fractions from SEC separation run on a 4-20% SDS-PAGE, samples 1-5 are from the $1^{st}$ elution peak and samples 6-9 are from the $2^{nd}$ elution peak.

FIG. 3A. SDS-PAGE of purified Trimeric-hArgI with an apparent MW of ~110 kDa. FIG. 3B. Incubations of trimeric-hArgI (●) or wt-hArgI (○) at 37° C. in pooled human serum, showing nearly identical stability over time.

DESCRIPTION OF ILLUSTRATIVE EMBODIMENTS

I. The Present Invention

Figure 1:
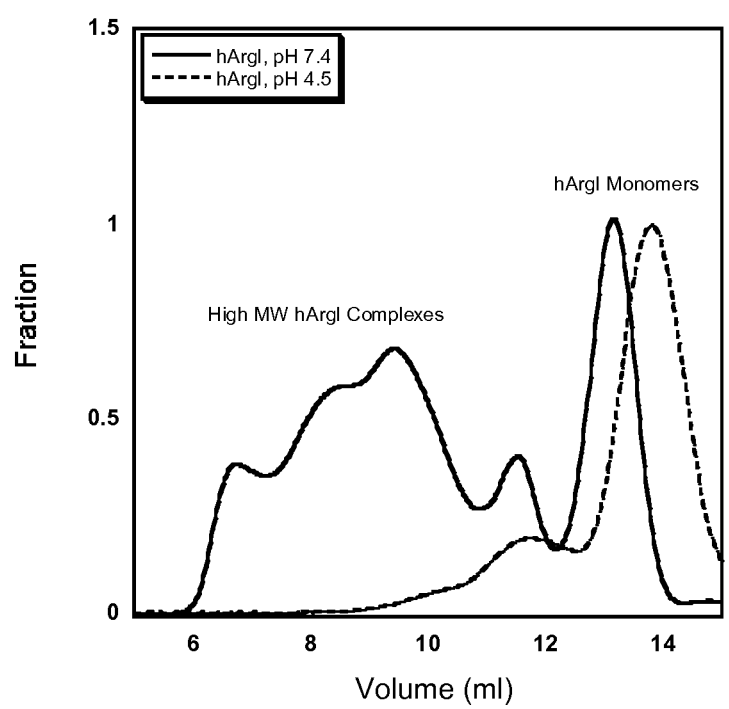
FIG. 1: Overlay of hArgI SEC at pH 7.4 (solid lines) and pH 4.5 (dashed lines). At physiological pH hArgI is primarily high molecular weight oligomers, but at pH 4.5 hArgI is primarily monomeric.
Figures 2A, 2B:
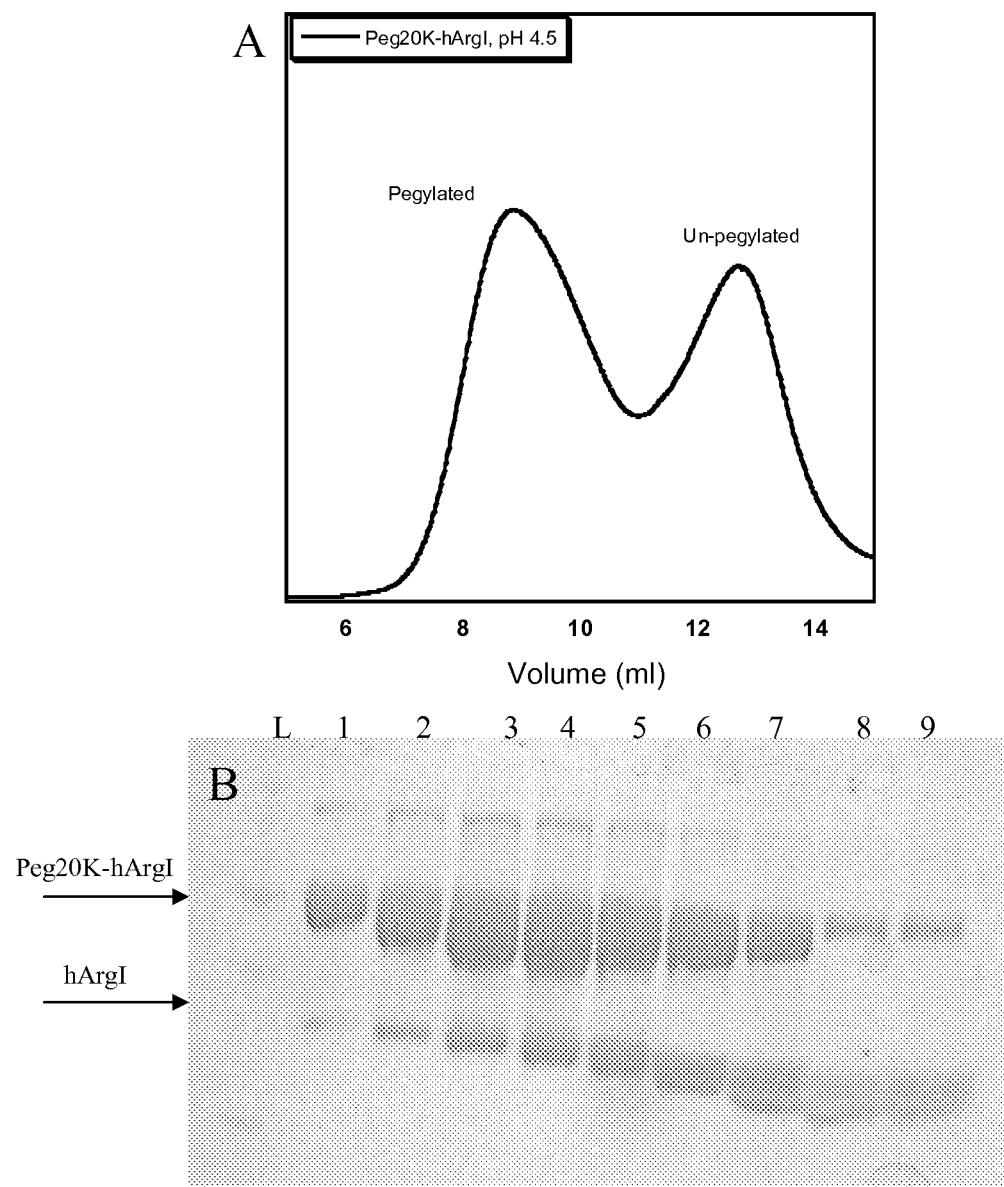
FIGS. 2A-B.

The present disclosure, according to certain embodiments, is generally directed to methods of preparing an arginase form that displays long circulation half life, such as a stabilized multimeric arginase or a purified pegylated arginase, and to constructs and compositions useful in such applications.

Without wishing to be bound by theory or mechanism, the present disclosure is based on the following studies. The inventors engineered a specific cysteine residue into the N-terminal of Arginase enabling site-specific pegylation with PEG 20,000 MW maleimide. Site specific pegylation results in the production of homogeneous material with well defined physical and chemical properties; they further devised a method for temporarily disrupting the multimeric state of Arginase allowing for efficient separation of site-specific pegylated Arginase from unreacted enzyme. Alternatively the inventors created a multimeric form of Arginase by fusing three subunits of enzyme together with flexible Gly-Ser linkers resulting in a stable high molecular weight complex with excellent kinetics and serum persistence. The multimeric Arginase is easily purified to homogeneity and does not require downstream bioprocessing steps of pegylation or separation of unconjugated material.

II. Definitions

As used herein, the term "half life" (½-life) refers to the time that would be required for the concentration of an arginase or a variant thereof to fall by half in vitro or in vivo, for example, after injection in a mammal.

As used herein the terms "protein" and "polypeptide" refer to compounds comprising amino acids joined via peptide bonds and are used interchangeably.

As used herein, the term "fusion protein" refers to a chimeric protein containing proteins or protein fragments (e.g., arginase or variants thereof) operably linked in a non-native way.

The terms "in operable combination," "in operable order" and "operably linked" refer to a linkage wherein the components so described are in a relationship permitting them to function in their intended manner, for example, a linkage of nucleic acid sequences in such a manner that a nucleic acid molecule capable of directing the transcription of a given gene and/or the synthesis of desired protein molecule, or a linkage of amino acid sequences in such a manner so that a fusion protein is produced.

By the term "linker" is meant to refer to a compound or moiety that acts as a molecular bridge to operably link two different molecules, wherein one portion of the linker is operably linked to a first molecule, and wherein another portion of the linker is operably linked to a second molecule.

The term "pegylated" refers to conjugation with polyethylene glycol (PEG), which has been widely used as a drug carrier, given its high degree of biocompatibility and ease of modification. PEG can be coupled (e.g., covalently linked) to active agents through the hydroxy groups at the end of the PEG chain via chemical methods; however, PEG itself is limited to at most two active agents per molecule. In a different approach, copolymer of PEG and amino acids have been explored as novel biomaterial which would retain the biocompatibility of PEG, but which would have the added advantage of numerous attachment points per molecule (thus providing greater drug loading), and which can be synthetically designed to suit a variety of applications.

The term "gene" refers to a DNA sequence that comprises control and coding sequences necessary for the production of a polypeptide or precursor thereof. The polypeptide can be encoded by a full length coding sequence or by any portion of the coding sequence so as the desired enzymatic activity is retained.

The term "wild-type" refers to the typical form of a gene, a gene product, or a characteristic of that gene or gene product when isolated from a naturally occurring source. A wild-type is that which is most frequently observed in a nature population and is thus arbitrarily designated the normal or wild-type form. In contrast, the term "modified," "variant," or "mutant" refers to a gene or gene product which displays modification in sequence and functional properties (i.e., altered characteristics) when compared to the wild-type gene or gene product. For example, arginase variants in the present invention may include stabilized arginase multimer or pegylated arginase. It is noted that naturally-occurring mutants can be isolated; there are identified by the fact that they have altered characteristics when compared to the wild-type gene or gene product.

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques (see, for example, Maniatis et al., 1988 and Ausubel et al., 1994, both incorporated herein by reference).

The term "expression vector" refers to any type of genetic construct comprising a nucleic acid coding for a RNA capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host cell. In addition to control sequences that govern transcription and translation, vectors and expression vectors may contain nucleic acid sequences that serve other functions as well and are described infra.

III. Arginase and Cancer Therapy

In certain aspects, the invention may be used for the treatment of cancers that require arginine for growth such as cancers that do not express (or are otherwise deficient in) argininosuccinate synthetase (ASS) or ornithine transcarbamylase, such as hepatocellular carcinoma, melanoma, and renal cell carcinoma, with engineered human enzymes that deplete L-Arginine and have been formulated for long serum persistence. The invention specifically discloses methods for preparing human Arginase variants engineered for increased circulation persistence.

B. Arginine Depletion for Cancer Therapy

Over the last fifty years, biochemical and clinical data have established that drastic reduction in the serum level of certain amino acids constitutes a promising strategy for the treatment of a variety of human cancers (Shen et al., 2006; Cellarier et al., 2003; Wetzler et al., 2007; Dinndorf et al., 2007). Malignant cells that fail to express amino acid biosynthetic genes are dependent on the plasma pool of that amino acid for growth. The administration of an enzyme that can efficiently degrade the particular amino acid in serum causes auxotrophic malignant cells to experience metabolic imbalances, inhibition of protein synthesis and irreversible cell cycle arrest, ultimately leading to cell death.

The in vitro anti-tumour activities of arginine depletion were reported (Scott et al., 2000; Wheatley et al., 2000). Of the 24 different tumour cell lines tested, which included common cancers such as breast, colorectal, lung, prostate and ovaries, all died within 5 days of arginine depletion. Using flow-cytometry studies, the group was able to show that normal cell lines would enter into quiescence for up to several weeks in G0 phase of the cell cycle without any apparent harm. Tumour cells, however, would proceed past the "R" point in the G1 phase and enter the S phase with deficiency of arginine. Without arginine, which is an irreplaceable amino acid, protein synthesis is deranged. Some cell lines were shown to die from apoptosis. More excitingly, repeated depletions can bring forth tumour kill without "resistance" being developed (Lamb et al., 2000).

Despite the promising in vitro data, attempts with arginine depletion to treat cancer in vivo were unsuccessful. Some attempts to treat tumour-bearing rats with intraperitoneal liver extracts met with no success (Storr & Burton, 1974). It is now generally recognized that under normal physiological condition, the blood plasma arginine level and indeed that of other amino acids too, are kept between the normal ranges (100-120 μM) with muscle being the main regulator. In the face of amino acid deficiency, intracellular protein breakdown pathways are activated (proteasomal and lysosomal) releasing amino acids into the circulation (Malumbres & Barbacid, 2001). This amino acid homeostatic mechanism keeps the various amino acid levels at constant ranges. Thus, previous attempts to deplete arginine with various physical methods or arginine degrading enzymes have failed because of the body's amino acid homeostatic mechanism.

C. Arginase

Arginase is a manganese-containing enzyme. It is the final enzyme of the urea cycle. Arginase is the fifth and final step in the urea cycle, a series of biophysical reactions in mammals during which the body disposes of harmful ammonia. Specifically, arginase converts L-arginine into L-ornithine and urea.

L-Arginine is the nitrogen donating substrate for nitric oxide synthase (NOS), producing L-Citrulline and NO. Although the $K_M$ of Arginase (2-5 mM) has been reported to be much higher than that of NOS for L-Arginine (2-20 μM), Arginase may also play a role in regulating NOS activity. Under certain conditions Arginase I is Cys-S-nitrosylated, resulting in higher affinity for L-Arginine and reduced availability of substrate for NOS.

Arginase is a homo-trimeric enzyme with an α/β fold of a parallel eight-stranded β-sheet surrounded by several helices. The enzyme contains a di-nuclear metal cluster that is integral to generating a hydroxide for nucleophilic attack on the guanidinium carbon of L-Arginine. The native metal for Arginase is $Mn^{2+}$. These $Mn^{2+}$ ions coordinate water, orientating and stabilizing the molecule and allowing water to act as a nucleophile and attack L-arginine, hydrolyzing it into ornithine and urea.

Mammals have two Arginase isozymes (EC 3.5.3.1) that catalyze the hydrolysis of L-Arginine to urea and L-Ornithine. The Arginase I gene is located on chromosome 6 (6q.23), is highly expressed in the cytosol of hepatocytes, and functions in nitrogen removal as the final step of the urea cycle. The Arginase II gene is found on chromosome 14 (14q.24.1). Arginase II is mitochondrially located in tissues such as kidney, brain, and skeletal muscle where it is thought to provide a supply of L-Ornithine for proline and polyamine biosynthesis (Lopez et al., 2005).

Arginases have been investigated for nearly 50 years as a method for degrading extracellular L-Arginine (Dillon et al., 2002). Some promising clinical results have been achieved by introducing Arginase into systemic circulation by transhepatic arterial embolisation; following which, several patients experienced partial remission of HCC (Cheng et al., 2005). However, since Arginase has a high $K_M$ (~2-5 mM) and exhibits very low activity at physiological pH values, high dosing is required for chemotherapeutic purposes (Dillon et al., 2002). While native Arginase is cleared from circulation within minutes (Savoca et al., 1984), a single injection of PEG-Arginase MW5000 in rats was sufficient to achieve near complete arginine depletion for ~3 days (Cheng et al., 2007).

Cheng et al. made the surprising observation that many human HCC cells lines do not express OTC (in addition to ASS) and thus they are susceptible to PEG-Arginase (Cheng et al., 2007). In mice implanted with Hep3b hepatocarcinoma cells weekly administration of PEG-Arginase resulted in tumor growth retardation which was accentuated by co-administration of 5-fluorouracil (5-FU). However, PEG-Arginase was used at the very high doses that are impractical for human therapy, reflecting its lower physiological activity.

To address these issues a bacterial arginine hydrolyzing enzyme, Arginine Deiminase or ADI which displays good kinetics and stability has been tested in vitro. A PEGylated form of ADI is now undergoing Phase II/III clinical trials. Unfortunately ADI is a bacterial enzyme and therefore it induces strong immune responses and adverse effects in most patients. However, for those patients that do not develop significant adverse responses, an impressive percentage exhibit stable disease or remission. Nonetheless because of its unfavorable immunological profile it is unlikely that L-Arginine depletion by ADI will become a mainstream treatment for liver cancer.

For clinical use, it is essential that the arginase is engineered to allow it to persist for long times (e.g., days) in circulation. In the absence of any modification, human arginase has a half life of only a few minutes in circulation primarily because its size is not sufficiently large to avoid filtration though the kidneys. Also the inventors have found that unmodified human Arginase is very susceptible to deactivation in serum and it is degraded with a half life of only four hours. Therefore, the present invention developed novel and improved forms of arginase for clinical research and potential therapeutic use with improved circulation persistence.

D. Arginase Variants of the Present Invention

Certain aspects of the present invention disclose compositions of matter for generating homogeneous arginase variants with increased molecular weight for long serum persistence, for example, stabilized multimeric arginase or pegylated arginase. Further aspects of the present invention also disclose methods for the generation of such variants that are amenable to bio-processing and scale-up, and novel formulations that result in the production of homogenous protein material and confer the desired pharmacokinetic and pharmacodynamic characteristics. Such Arginase variants and associated methods are described in detail in later sections.

IV. Conjugates

Compositions and methods of the present invention involve stabilized multimeric arginase comprising multiple arginase monomers conjugated to form the stabilized arginase. The multimeric arginase may be chemically conjugated, crosslinked, or fused at the protein level using conventional methods.

B. Fusion Proteins

Certain embodiments of the present invention concern fusion proteins. These molecules generally have three arginase monomer subunits linked at the N- or C-terminus. For example, fusions may also employ leader sequences from other species to permit the recombinant expression of a protein in a heterologous host. Another useful fusion includes the addition of six histidine residues or an immunologically active domain, such as an antibody epitope, to facilitate purification of the fusion protein.

Methods of generating fusion proteins are well known to those of skill in the art. Such proteins can be produced, for example, by de novo synthesis of the complete fusion protein, or by attachment of three DNA sequences encoding the arginase monomer, followed by expression of the intact fusion protein.

Production of fusion proteins that recover the functional activities of the parent proteins may be facilitated by connecting genes with a bridging DNA segment encoding a peptide linker that is spliced between the polypeptides connected in tandem. The linker would be of sufficient length to allow proper folding of the resulting fusion protein.

C. Linkers

In certain embodiments, the multimeric arginase may be chemical conjugated using bifunctional cross-linking reagents or fused at the protein level with peptide linkers.

Bifunctional cross-linking reagents have been extensively used for a variety of purposes including preparation of affinity matrices, modification and stabilization of diverse structures, identification of ligand and receptor binding sites, and structural studies. Suitable peptide linkers may also be used to link the arginase monomers in the present invention, such as Gly-Ser linkers.

Homobifunctional reagents that carry two identical functional groups proved to be highly efficient in inducing cross-linking between identical and different macromolecules or subunits of a macromolecule, and linking of polypeptide ligands to their specific binding sites. Heterobifunctional reagents contain two different functional groups. By taking advantage of the differential reactivities of the two different functional groups, cross-linking can be controlled both selectively and sequentially. The bifunctional cross-linking reagents can be divided according to the specificity of their functional groups, e.g., amino, sulfhydryl, guanidino, indole, carboxyl specific groups. Of these, reagents directed to free amino groups have become especially popular because of their commercial availability, ease of synthesis and the mild reaction conditions under which they can be applied.

A majority of heterobifunctional cross-linking reagents contains a primary amine-reactive group and a thiol-reactive group. In another example, heterobifunctional cross-linking reagents and methods of using the cross-linking reagents are described (U.S. Pat. No. 5,889,155, specifically incorporated herein by reference in its entirety). The cross-linking reagents combine a nucleophilic hydrazide residue with an electrophilic maleimide residue, allowing coupling in one example, of aldehydes to free thiols. The cross-linking reagent can be modified to cross-link various functional groups.

Additionally, any other linking/coupling agents and/or mechanisms know to those of skill in the art may be used to combine human arginase of the present invention, such as, for example, antibody-antigen interaction, avidin biotin linkages, amide linkages, ester linkages, thioester linkages, ether linkages, thioether linkages, phosphoester linkages, phosphoramide linkages, anhydride linkages, disulfide linkages, ionic and hydrophobic interactions, bispecific antibodies and antibody fragments, or combinations thereof.

It is preferred that a cross-linker having reasonable stability in blood will be employed. Numerous types of disulfide-bond containing linkers are known that can be successfully employed to conjugate targeting and therapeutic/preventative agents. Linkers that contain a disulfide bond that is sterically hindered may prove to give greater stability in vivo. These linkers are thus one group of linking agents.

In addition to hindered cross-linkers, non-hindered linkers also can be employed in accordance herewith. Other useful cross-linkers, not considered to contain or generate a protected disulfide, include SATA, SPDP and 2-iminothiolane (Wawrzynczak & Thorpe, 1987). The use of such cross-linkers is well understood in the art. Another embodiment involves the use of flexible linkers.

Once chemically conjugated, the peptide generally will be purified to separate the conjugate from unconjugated agents and from other contaminants. A large number of purification techniques are available for use in providing conjugates of a sufficient degree of purity to render them clinically useful.

Purification methods based upon size separation, such as gel filtration, gel permeation or high performance liquid chromatography, will generally be of most use. Other chromatographic techniques, such as Blue-Sepharose separation, may also be used. Conventional methods to purify the fusion proteins from inclusion bodies may be useful for the present invention, such as using weak detergents like sodium N-lauroyl-sarcosine (SLS).

V. Pegylation

In certain aspects of the invention, methods and compositions related to pegylated arginase are disclosed. Specifically, pegylation of arginase at an engineered cysteine residue (e.g., substituting the third residue of the N-terminal) may be used to produce a homogenous pegylated arginase composition. Methods for isolation of pegylated arginase based on temporary disruption of polymerization are also disclosed.

Pegylation is the process of covalent attachment of poly (ethylene glycol) polymer chains to another molecule, normally a drug or therapeutic protein. Pegylation is routinely achieved by incubation of a reactive derivative of PEG with the target macromolecule. The covalent attachment of PEG to a drug or therapeutic protein can "mask" the agent from the host's immune system (reduced immunogenicity and antigenicity), increase the hydrodynamic size (size in solution) of the agent which prolongs its circulatory time by reducing renal clearance. Pegylation can also provide water solubility to hydrophobic drugs and proteins.

The first step of the pegylation is the suitable functionalization of the PEG polymer at one or both terminals. PEGs that are activated at each terminus with the same reactive moiety are known as "homobifunctional", whereas if the functional groups present are different, then the PEG derivative is referred as "heterobifunctional" or "heterofunctional." The chemically active or activated derivatives of the PEG polymer are prepared to attach the PEG to the desired molecule.

The choice of the suitable functional group for the PEG derivative is based on the type of available reactive group on the molecule that will be coupled to the PEG. For proteins, typical reactive amino acids include lysine, cysteine, histidine, arginine, aspartic acid, glutamic acid, serine, threonine, tyrosine. The N-terminal amino group and the C-terminal carboxylic acid can also be used.

The techniques used to form first generation PEG derivatives are generally reacting the PEG polymer with a group that is reactive with hydroxyl groups, typically anhydrides, acid chlorides, chloroformates and carbonates. In the second generation pegylation chemistry more efficient functional groups such as aldehyde, esters, amides etc made available for conjugation.

As applications of pegylation have become more and more advanced and sophisticated, there has been an increase in need for heterobifunctional PEGs for conjugation. These heterobifunctional PEGs are very useful in linking two entities, where a hydrophilic, flexible and biocompatible spacer is needed. Preferred end groups for heterobifunctional PEGs are maleimide, vinyl sulfones, pyridyl disulfide, amine, carboxylic acids and NHS esters.

The most common modification agents, or linkers, are based on methoxy PEG (mPEG) molecules. Their activity depends on adding a protein-modifying group to the alcohol end. In some instances polyethylene glycol (PEG diol) is used as the precursor molecule. The diol is subsequently modified at both ends in order to make a hetero- or homo-dimeric PEG-linked molecule (as shown in the example with PEG bis-vinylsulfone).

Proteins are generally PEGylated at nucleophilic sites such as unprotonated thiols (cysteinyl residues) or amino groups. Examples of cysteinyl-specific modification reagents include PEG maleimide, PEG iodoacetate, PEG thiols, and PEG vinylsulfone. All four are strongly cysteinyl-specific under mild conditions and neutral to slightly alkaline pH but each has some drawbacks. The amide formed with the maleimides can be somewhat unstable under alkaline conditions so there may be some limitation to formulation options with this linker. The amide linkage formed with iodo PEGs is more stable, but free iodine can modify tyrosine residues under some conditions. PEG thiols form disulfide bonds with protein thiols, but this linkage can also be unstable under alkaline conditions. PEG-vinylsulfone reactivity is relatively slow compared to maleimide and iodo PEG; however, the thioether linkage formed is quite stable. Its slower reaction rate also can make the PEG-vinylsulfone reaction easier to control.

Site-specific pegylation at native cysteinyl residues is seldom carried out, since these residues are usually in the form of disulfide bonds or are required for biological activity. On the other hand, site-directed mutagenesis can be used to incorporate cysteinyl pegylation sites for thiol-specific linkers. The cysteine mutation must be designed such that it is accessible to the pegylation reagent and is still biologically active after pegylation.

Amine-specific modification agents include PEG NHS ester, PEG tresylate, PEG aldehyde, PEG isothiocyanate, and several others. All react under mild conditions and are very specific for amino groups. The PEG NHS ester is probably one of the more reactive agents; however, its high reactivity can make the pegylation reaction difficult to control at large scale. PEG aldehyde forms an imine with the amino group, which is then reduced to a secondary amine with sodium cyanoborohydride. Unlike sodium borohydride, sodium cyanoborohydride will not reduce disulfide bonds. However; this chemical is highly toxic and must be handled cautiously, particularly at lower pH where it becomes volatile.

Due to the multiple lysine residues on most proteins, site-specific pegylation can be a challenge. Fortunately, because these reagents react with unprotonated amino groups, it is possible to direct the pegylation to lower-pK amino groups by performing the reaction at a lower pH. Generally the pK of the alpha-amino group is 1-2 pH units lower than the epsilon-amino group of lysine residues. By PEGylating the molecule at pH 7 or below, high selectivity for the N-terminus frequently can be attained. However; this is only feasible if the N-terminal portion of the protein is not required for biological activity. Still, the pharmacokinetic benefits from pegylation frequently outweigh a significant loss of in vitro bioactivity, resulting in a product with much greater in vivo bioactivity regardless of pegylation chemistry.

There are several parameters to consider when developing a pegylation procedure. Fortunately, there are usually no more than four or five key parameters. The "design of experiments" approach to optimization of pegylation conditions can be very useful. For thiol-specific pegylation reactions, parameters to consider include: protein concentration, PEG-to-protein ratio (on a molar basis), temperature, pH, reaction time, and in some instances, the exclusion of oxygen. (Oxygen can contribute to intermolecular disulfide formation by the protein, which will reduce the yield of the PEGylated product.) The same factors should be considered (with the exception of oxygen) for amine-specific modification except that pH may be even more critical, particularly when targeting the N-terminal amino group.

For both amine- and thiol-specific modifications, the reaction conditions may affect the stability of the protein. This may limit the temperature, protein concentration, and pH. In addition, the reactivity of the PEG linker should be known before starting the pegylation reaction. For example, if the pegylation agent is only 70 percent active, the amount of PEG used should ensure that only active PEG molecules are counted in the protein-to-PEG reaction stoichiometry. How to determine PEG reactivity and quality will be described later.

VI. Proteins and Peptides

In certain embodiments, the present invention concerns novel compositions comprising at least one protein or peptide, such as stabilized arginase multimers. These peptides may be comprised in a fusion protein or conjugated to an agent as described supra.

B. Proteins and Peptides

As used herein, a protein or peptide generally refers, but is not limited to, a protein of greater than about 200 amino acids, up to a full length sequence translated from a gene; a polypeptide of greater than about 100 amino acids; and/or a peptide of from about 3 to about 100 amino acids. For convenience, the terms "protein," "polypeptide" and "peptide are used interchangeably herein.

In certain embodiments the size of at least one protein or peptide may comprise, but is not limited to, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, about 110, about 120, about 130, about 140, about 150, about 160, about 170, about 180, about 190, about 200, about 210, about 220, about 230, about 240, about 250, about 275, about 300, about 325, about 350, about 375, about 400, about 425, about 450, about 475, about 500, about 525, about 550, about 575, about 600, about 625, about 650, about 675, about 700, about 725, about 750, about 775, about 800, about 825, about 850, about 875, about 900, about 925, about 950, about 975, about 1000, about 1100, about 1200, about 1300, about 1400, about 1500, about 1750, about 2000, about 2250, about 2500 or greater amino acid residues.

As used herein, an "amino acid residue" refers to any naturally occurring amino acid, any amino acid derivative or any amino acid mimic known in the art. In certain embodiments, the residues of the protein or peptide are sequential, without any non-amino acid interrupting the sequence of amino acid residues. In other embodiments, the sequence may comprise one or more non-amino acid moieties. In particular embodiments, the sequence of residues of the protein or peptide may be interrupted by one or more non-amino acid moieties.

Accordingly, the term "protein or peptide" encompasses amino acid sequences comprising at least one of the 20 common amino acids found in naturally occurring proteins, or at least one modified or unusual amino acid, including but not limited to those shown on Table 1 below.

TABLE 1

Modified and Unusual Amino Acids

| Abbr. | Amino Acid | Abbr. | Amino Acid |
|---|---|---|---|
| Aad | 2-Aminoadipic acid | EtAsn | N-Ethylasparagine |
| Baad | 3-Aminoadipic acid | Hyl | Hydroxylysine |
| Bala | β-alanine, β-Amino-propionic acid | AHyl | allo-Hydroxylysine |
| Abu | 2-Aminobutyric acid | 3Hyp | 3-Hydroxyproline |
| 4Abu | 4-Aminobutyric acid, piperidinic acid | 4Hyp | 4-Hydroxyproline |
| Acp | 6-Aminocaproic acid | Ide | Isodesmosine |
| Ahe | 2-Aminoheptanoic acid | AIle | allo-Isoleucine |
| Aib | 2-Aminoisobutyric acid | MeGly | N-Methylglycine, sarcosine |
| Baib | 3-Aminoisobutyric acid | MeIle | N-Methylisoleucine |
| Apm | 2-Aminopimelic acid | MeLys | 6-N-Methyllysine |
| Dbu | 2,4-Diaminobutyric acid | MeVal | N-Methylvaline |
| Des | Desmosine | Nva | Norvaline |
| Dpm | 2,2'-Diaminopimelic acid | Nle | Norleucine |
| Dpr | 2,3-Diaminopropionic acid | Orn | Ornithine |
| EtGly | N-Ethylglycine | | |

Proteins or peptides may be made by any technique known to those of skill in the art, including the expression of proteins, polypeptides or peptides through standard molecular biological techniques, the isolation of proteins or peptides from natural sources, or the chemical synthesis of proteins or peptides. The nucleotide and protein, polypeptide and peptide sequences corresponding to various genes have been previously disclosed, and may be found at computerized databases known to those of ordinary skill in the art. One such database is the National Center for Biotechnology Information's Genbank and GenPept databases (http://www.ncbi.nlm.nih.gov/). The coding regions for known genes may be amplified and/or expressed using the techniques disclosed herein or as would be know to those of ordinary skill in the art. Alternatively, various commercial preparations of proteins, polypeptides and peptides are known to those of skill in the art.

C. Nucleic Acids and Vectors

In certain aspects of the invention, nucleic acid sequences encoding a fusion protein as a stabilized multimeric arginase may be disclosed. Depending on which expression system to be used, nucleic acid sequences can be selected based on conventional methods. For example, human arginase I and II contain multiple codons that are rarely utilized in *E. coli* that may interfere with expression, therefore the respective genes or variants thereof may be codon optimized for *E. coli* expression. Various vectors may be also used to express the protein of interest, such as a fusion multimeric arginase or a cysteine-substituted arginase. Exemplary vectors include, but are not limited, plasmid vectors, viral vectors, transposon or liposome-based vectors.

D. Host Cells

Host cells, preferably eukaryotic cells, useful in the present invention are any that may be transformed to allow the expression and secretion of arginase and fusion multimers thereof. The host cells may be bacteria, mammalian cells, yeast, or filamentous fungi. Various bacteria include *Escherichia* and *Bacillus*. Yeasts belonging to the genera *Saccharomyces, Kluyveromyces, Hansenula,* or *Pichia* would find use as an appropriate host cell. Various species of filamentous fungi may be used as expression hosts including the following genera: *Aspergillus, Trichoderma, Neurospora, Penicillium, Cephalosporium, Achlya, Podospora, Endothia, Mucor, Cochliobolus* and *Pyricularia*.

Examples of usable host organisms include bacteria, e.g., *Escherichia coli* MC1061, derivatives of *Bacillus subtilis* BRB1 (Sibakov et al., 1984), *Staphylococcus aureus* SAI123 (Lordanescu, 1975) or *Streptococcus lividans* (Hopwood et al., 1985); yeasts, e.g., *Saccharomyces cerevisiae* AH 22 (Mellor et al., 1983) and *Schizosaccharomyces pombe*; filamentous fungi, e.g., *Aspergillus nidulans, Aspergillus awamori* (Ward, 1989), *Trichoderma reesei* (Penttila et al., 1987; Harkki et al, 1989).

Examples of mammalian host cells include Chinese hamster ovary cells (CHO-K1; ATCC CCL61), rat pituitary cells ($GH_1$; ATCC CCL82), HeLa S3 cells (ATCC CCL2.2), rat hepatoma cells (H-4-II-E; ATCCCRL 1548) SV40-transformed monkey kidney cells (COS-1; ATCC CRL 1650) and murine embryonic cells (NIH-3T3; ATCC CRL 1658). The foregoing being illustrative but not limitative of the many possible host organisms known in the art. In principle, all hosts capable of secretion can be used whether prokaryotic or eukaryotic.

Mammalian host cells expressing the arginase and/or their fusion multimers are cultured under conditions typically employed to culture the parental cell line. Generally, cells are cultured in a standard medium containing physiological salts and nutrients, such as standard RPMI, MEM, IMEM or DMEM, typically supplemented with 5-10% serum, such as fetal bovine serum. Culture conditions are also standard, e.g., cultures are incubated at 37° C. in stationary or roller cultures until desired levels of the proteins are achieved.

E. Protein Purification

Protein purification techniques are well known to those of skill in the art. These techniques involve, at one level, the homogenization and crude fractionation of the cells, tissue or organ to polypeptide and non-polypeptide fractions. The protein or polypeptide of interest may be further purified using chromatographic and electrophoretic techniques to achieve partial or complete purification (or purification to homogeneity) unless otherwise specified. Analytical methods particularly suited to the preparation of a pure peptide are ion-exchange chromatography, gel exclusion chromatography, polyacrylamide gel electrophoresis, affinity chromatography, immunoaffinity chromatography and isoelectric focusing. A particularly efficient method of purifying peptides is fast performance liquid chromatography (FPLC) or even high performance liquid chromatography (HPLC).

A purified protein or peptide is intended to refer to a composition, isolatable from other components, wherein the protein or peptide is purified to any degree relative to its naturally-obtainable state. An isolated or purified protein or peptide, therefore, also refers to a protein or peptide free from the environment in which it may naturally occur. Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95%, or more of the proteins in the composition.

Various techniques suitable for use in protein purification are well known to those of skill in the art. These include, for example, precipitation with ammonium sulphate, PEG, antibodies and the like, or by heat denaturation, followed by: centrifugation; chromatography steps such as ion exchange, gel filtration, reverse phase, hydroxylapatite and affinity chromatography; isoelectric focusing; gel electrophoresis; and combinations of these and other techniques. As is generally known in the art, it is believed that the order of conducting the various purification steps may be changed, or that certain steps may be omitted, and still result in a suitable method for the preparation of a substantially purified protein or peptide.

Various methods for quantifying the degree of purification of the protein or peptide are known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity therein, assessed by a "-fold purification number." The actual units used to represent the amount of activity will, of course, be dependent upon the particular assay technique chosen to follow the purification, and whether or not the expressed protein or peptide exhibits a detectable activity.

There is no general requirement that the protein or peptide always be provided in their most purified state. Indeed, it is contemplated that less substantially purified products may have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

In certain embodiments a protein or peptide may be isolated or purified, for example, a stabilized arginase multimeric fusion protein, or an arginase prior or post pegylation. For example, a His tag or an affinity epitope may be comprised in such a arginase variant to facilitate purification. Affinity chromatography is a chromatographic procedure that relies on the specific affinity between a substance to be isolated and a molecule to which it can specifically bind. This is a receptor-ligand type of interaction. The column material is synthesized by covalently coupling one of the binding partners to an insoluble matrix. The column material is then able to specifically adsorb the substance from the solution. Elution occurs by changing the conditions to those in which binding will not occur (e.g., altered pH, ionic strength, temperature, etc.). The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand.

In a further aspect, methods for isolating pegylated arginase from unpegylated arginase are also disclosed by using a low pH condition, such as in the range of about 3 to about 5.5. Such a low pH may greatly reduce monomeric form of unpegylated arginase, therefore allowing good separation of high molecular weight pegylated arginase from unpegylated monomeric arginase. Purification methods based upon size separation, such as size exclusion chromatography (such as gel filtration), gel permeation or high performance liquid chromatography, will generally be of most use.

Size exclusion chromatography (SEC) is a chromatographic method in which molecules in solution are separated based on their size, or in more technical terms, their hydrodynamic volume. It is usually applied to large molecules or macromolecular complexes such as proteins and industrial polymers. Typically, when an aqueous solution is used to transport the sample through the column, the technique is known as gel filtration chromatography, versus the name gel permeation chromatography which is used when an organic solvent is used as a mobile phase.

The underlying principle of SEC is that particles of different sizes will elute (filter) through a stationary phase at different rates. This results in the separation of a solution of particles based on size. Provided that all the particles are loaded simultaneously or near simultaneously, particles of the same size should elute together. Each size exclusion column has a range of molecular weights that can be separated. The exclusion limit defines the molecular weight at the upper end of this range and is where molecules are too large to be trapped in the stationary phase. The permeation limit defines the molecular weight at the lower end of the range of separation and is where molecules of a small enough size can penetrate into the pores of the stationary phase completely and all molecules below this molecular mass are so small that they elute as a single band.

High-performance liquid chromatography (or High pressure liquid chromatography, HPLC) is a form of column chromatography used frequently in biochemistry and analytical chemistry to separate, identify, and quantify compounds. HPLC utilizes a column that holds chromatographic packing material (stationary phase), a pump that moves the mobile phase(s) through the column, and a detector that shows the retention times of the molecules. Retention time varies depending on the interactions between the stationary phase, the molecules being analyzed, and the solvent(s) used.

VII. Arginase Cofactor

A cofactor is a non-protein chemical compound that is bound (either tightly or loosely) to a protein and is required for the protein's biological activity. These proteins are commonly enzymes and cofactors can be considered "helper molecules/ions" that assist in biochemical transformations. Metal ions are common cofactors. In humans this list commonly includes iron, manganese, cobalt, copper, zinc, selenium, and molybdenum Arginase with the native metal cofactor (i.e., $Mn^{2+}$) exhibits a pH optimum of 9. At physiological pH the enzyme exhibit more than 10-fold lower $k_{cat}/K_m$ in the hydrolysis of L-Arginine. The low catalytic activity displayed by the wild-type human arignase with the native $Mn^{2+}$ cofactor presents a problem for human therapy since it means that impractical doses of the enzyme have to be used to achieve a therapeutically relevant reduction in L-Arginine plasma levels.

The inventors contemplated that that substitution of the native metal ($Mn^{2+}$) with other divalent cations might be exploited to shift under the pH optimum of the enzyme to a lower value and thus achieve high rates of L-Arginine hydrolysis under physiological conditions.

As disclosed in the U.S. provisional patent application No. 61/110,218, which is incorporated by reference herewith, the inventors have improved the kinetic and stability of human Arginase (h-Arg) by replacing the Mn(II) cofactor of the catalytic center with another metal, for example, cobalt (II). The hArg-$Co^2$ variants were shown to display cancer cytotoxicity more than 10-15 fold higher than the authentic hArg which contains Mn(II) which are equal to or exceed those of ADI.

In certain aspects of the present invention, the multimeric arginase or pegylated arginase may comprise a non-native metal cofactor, such as cobalt. For example, the desired divalent metal cation may be incorporated into stabilized multimeric arginase by incubating with 10 mM metal, such as $CoCl_2$.

VIII. Pharmaceutical Compositions

Where clinical applications are contemplated, it may be necessary to prepare pharmaceutical compositions—expression vectors, virus stocks, proteins, antibodies and drugs—in a form appropriate for the intended application. Generally, pharmaceutical compositions of the present invention comprise an effective amount of one or more arginase variants or additional agent dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of an pharmaceutical composition that contains at least one arginase variant, such as a stabilized multimeric arginase or a pegylated arginase isolated by the method disclosed herein, or additional active ingredient will be known to those of skill in the art in light of the present disclosure, as exemplified by Remington's Pharmaceutical Sciences, $18^{th}$ Ed., 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, $18^{th}$ Ed., 1990, incorporated herein by reference). Except insofar as any conventional carrier is incompatible with the active ingredient, its use in the pharmaceutical compositions is contemplated.

The present invention may comprise different types of carriers depending on whether it is to be administered in solid, liquid or aerosol form, and whether it need to be sterile for such routes of administration as injection. The present invention can be administered intravenously, intradermally, transdermally, intrathecally, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in lipid compositions (e.g., liposomes), or by other method or any combination of the forgoing as would be known to one of ordinary skill in the art (see, for example, Remington's Pharmaceutical Sciences, $18^{th}$ Ed., 1990, incorporated herein by reference).

The arginase variants may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentary administrations such as drug release capsules and the like.

Further in accordance with the present invention, the composition of the present invention suitable for administration is provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of a the composition contained therein, its use in administrable composition for use in practicing the methods of the present invention is appropriate. Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In accordance with the present invention, the composition is combined with the carrier in any convenient and practical manner, i.e., by solution, suspension, emulsification, admixture, encapsulation, absorption and the like. Such procedures are routine for those skilled in the art.

In a specific embodiment of the present invention, the composition is combined or mixed thoroughly with a semi-solid or solid carrier. The mixing can be carried out in any convenient manner such as grinding. Stabilizing agents can be also added in the mixing process in order to protect the composition from loss of therapeutic activity, i.e., denaturation in the stomach. Examples of stabilizers for use in an the composition include buffers, amino acids such as glycine and lysine, carbohydrates such as dextrose, mannose, galactose, fructose, lactose, sucrose, maltose, sorbitol, mannitol, etc.

In further embodiments, the present invention may concern the use of a pharmaceutical lipid vehicle compositions that include arginase variants, one or more lipids, and an aqueous solvent. As used herein, the term "lipid" will be defined to include any of a broad range of substances that is characteristically insoluble in water and extractable with an organic solvent. This broad class of compounds are well known to those of skill in the art, and as the term "lipid" is used herein, it is not limited to any particular structure. Examples include compounds which contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods of the present invention.

One of ordinary skill in the art would be familiar with the range of techniques that can be employed for dispersing a composition in a lipid vehicle. For example, the stabilized multimeric arginase or pegylated arginase may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition of the present invention administered to an animal patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

IX. Kits

The present invention provides kits, such as therapeutic kits. For example, a kit may comprise one or more pharmaceutical composition as described herein and optionally instructions for their use. Kits may also comprise one or more devices for accomplishing administration of such compositions. For example, a subject kit may comprise a pharmaceutical composition and catheter for accomplishing direct intravenous injection of the composition into a cancerous tumor. In other embodiments, a subject kit may comprise pre-filled ampoules of a stabilized multimeric arginase or isolated pegylated arginase, optionally formulated as a pharmaceutical, or lyophilized, for use with a delivery device.

Kits may comprise a container with a label. Suitable containers include, for example, bottles, vials, and test tubes. The containers may be formed from a variety of materials such as glass or plastic. The container may hold a composition which includes an antibody that is effective for therapeutic or non-therapeutic applications, such as described above. The label on the container may indicate that the composition is used for a specific therapy or non-therapeutic application, and may also indicate directions for either in vivo or in vitro use, such as those described above. The kit of the invention will typically comprise the container described above and one or more other containers comprising materials desirable from a commercial and user standpoint, including buffers, diluents, filters, needles, syringes, and package inserts with instructions for use.

X. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Introduction of N-Terminal Cys Residue, Purification and Pegylation

The inventors constructed a nucleotide sequence containing an *E. coli* codon optimized gene of human Arginase I (hArgI) prefaced with a codon for Cys on the third residue and a 6×His tag for ease of purification (Called NTC-hArgI; SEQ ID NO:2 encoding an amino acid sequence as set forth in SEQ ID NO:1). After cloning into a pET28a vector (Novagen), *E. coli* (BL21) containing an appropriate Arginase expression vector were grown at 37° C. using Terrific Broth (TB) media containing 50 μg/ml kanamycin in shake flasks at 250 rpm until reaching an $OD_{600}$ of 0.5-0.6. At that point the cultures were transferred to 25° C. and induced with 0.5 mM IPTG and allowed to express protein for an additional 12 hrs. Cell pellets were then collected by centrifugation and re-suspended in an IMAC buffer (10 mM $NaPO_4$/10 mM imidazole/300 mM NaCl, pH 8). After lysis by a French pressure cell, lysates were centrifuged at 20,000×g for 20 min at 4° C., and the resulting supernatant applied to a cobalt immobilized metal-ion affinity chromatography (IMAC) column, washed with 80-90 column volumes of an IMAC buffer containing 0.1% Triton 114, 10-20 column volumes of IMAC buffer, and then eluted with an IMAC elution buffer (50 mM $NaPO_4$/250 mM imidazole/300 mM NaCl, pH 8). NTC-hArgI was then buffer exchanged into a 20 mM $NaPO_4$, 100 mM NaCl buffer at pH 6.8 using a 10,000 MWCO filtration device (Amicon). Using a small reaction jar Tris (2-carboxyethyl) phosphine (Molecular Probes) is added to NTC-hArgI at 6-8 molar equivalents and allowed to react 30-40 min under stirring at 25° C. to reduce any oxidized thiols. Three molar equivalents of Methoxy PEG Maleimide MW 20,000 (Peg20K) (Jenkem Technologies) are added and allowed to react for 1 hr at 25° C. Native ArgI contains three cysteine residues that are relatively buried in the interior of the protein while the introduced N-terminal cysteine is solvent exposed. The N-terminal cysteine is preferentially pegylated in this manner, although large molar excesses of Peg20K will pegylate the native cysteine residues. Using ~3 molar equiv of Peg20K will conjugate 40-50% of NTC-hArgI with minimal native cysteine conjugation.

Example 2

Separation of Pegylated and Unpegylated hArgI

Size exclusion chromatography is commonly employed to separate pegylated proteins from unreacted material. However the separation of pegylated hArgI from the native enzyme has proven problematic due to the high oligomerization propensity of hArgI. Separations on a Superdex 200 column (Pharmacia Biotech) using PBS pH 7.4 as a mobile phase revealed that hArgI is present in a variety of oligomeric states ranging from trimers to nonamers resulting in poor separation of pegylated material. Likewise a sephacryl S-500 (GE Healthcare) did not result in any better resolution. The inventors therefore engineered an E256Q mutation into the NTC-hArgI coding sequence. The E256Q mutant was previously shown to exist as a monomer with near wild-type activity (Sabio et al., 2001). The inventors' gel filtration experiments with this variant showed that it exists mainly as monomers and dimers with no observable higher order oligomerization. After conjugation of this variant with Peg20K, the inventors were able to get homogeneous separation on a Superdex 200 column in a PBS pH 7.4 mobile phase buffer. However, monomeric forms of hArgI are greatly reduced in stability rendering this variant unusable as a drug candidate.

Recognizing that E256 makes an ionic bond with R255 from an adjacent subunit the inventors hypothesized that protonating E256 would disrupt that bond and transiently mimic the E256Q monomeric variant. Using a Superdex 200 column equilibrated with a sodium acetate buffer at pH 4.5 the inventors were able to reduce the high order oligomers down to ~90% monomeric and ~10% dimeric (FIG. 1). This method allows good separation of Peg20K-hArgI from non-pegylated hArgI Example 3

Creation of a Multimeric Human ArginaseI

The active and predominant oligomeric state of hArgI is the trimeric form (MW ~105,000 Da). However in circulation, dissociation into the 35,000 Da monomer subunits results in a species that is below the cut-off for renal filtration which in turn results in renal clearance within minutes. The trimer-monomer equilibrium thus adversely impacts the half-life of hArg in mammalian circulation. To overcome the circulatory clearance the inventors created a trimeric hArgI fusion protein connected by flexible Gly/Ser linkers (SEQ ID NO:3), which is stabilized in the trimeric form in circulation.

Nucleic acid sequences encoding trimeric hArgI fusion protein (SEQ ID NO:4) was constructed in several stages, such that the coding sequence for each hArgI subunit (hArgI 1-3) was cloned separately into a pET28a vector for sequence verification before consolidation as a fusion protein in a single pET28a vector.

hArgI-1

Using an *E. coli* codon optimized gene as a template and oligonucleotides (IDT) coding for a poly Gly-Ser tract, the inventors constructed the first hArgI subunit with an N-terminal NcoI restriction site, codons for a 6×His tag, removed the stop codon such that the C-terminal was contiguous with a (Gly-Ser)$_{10}$ linker (GSGSGSGSGSGSGSGSGSGS; SEQ ID NO:5) followed by an EcoRI restriction site. After cloning into a pET28a plasmid, the sequence was verified to be free of undesired mutations.

hArgI-2

Using an *E. coli* codon optimized gene as a template and oligonucleotides (IDT) coding for a poly Gly$_2$-Ser$_2$ tract, the inventors constructed the second hArgI subunit with an N-terminal EcoRI restriction site, removed the stop codon such that the C-terminal was contiguous with a (Gly$_2$-Ser$_2$)$_5$ linker (GGSSGGSSGGSSGGSSGGSS; SEQ ID NO:6) followed by an in frame BamHI restriction site followed by an in frame NotI restriction site. After cloning in between EcoRI and NotI in pET28a, the sequence was verified to be free of undesired mutations.

hArgI-3

Using an *E. coli* codon optimized gene as a template and oligonucleotides (IDT), the inventors constructed the third hArgI subunit with an N-terminal BamHI restriction site, a C-terminal stop codon, and a NotI restriction site. After cloning in between BamHI and NotI in pET28a, the sequence was verified to be free of undesired mutations.

Trimeric-hArgI Assembly

The gene for the second subunit was digested from the hArgI-2 plasmid with EcoRI and NotI and gel purified. This was then ligated C-terminal to the hArgI-1 plasmid that had been digested with EcoRI and NotI. The gene for the third subunit was digested from the hArgI-3 plasmid with BamHI and NotI and gel purified. The plasmid containing the first two subunits was digested with BamHI and NotI and ligated with the third subunit.

Figures 3A, 3B:
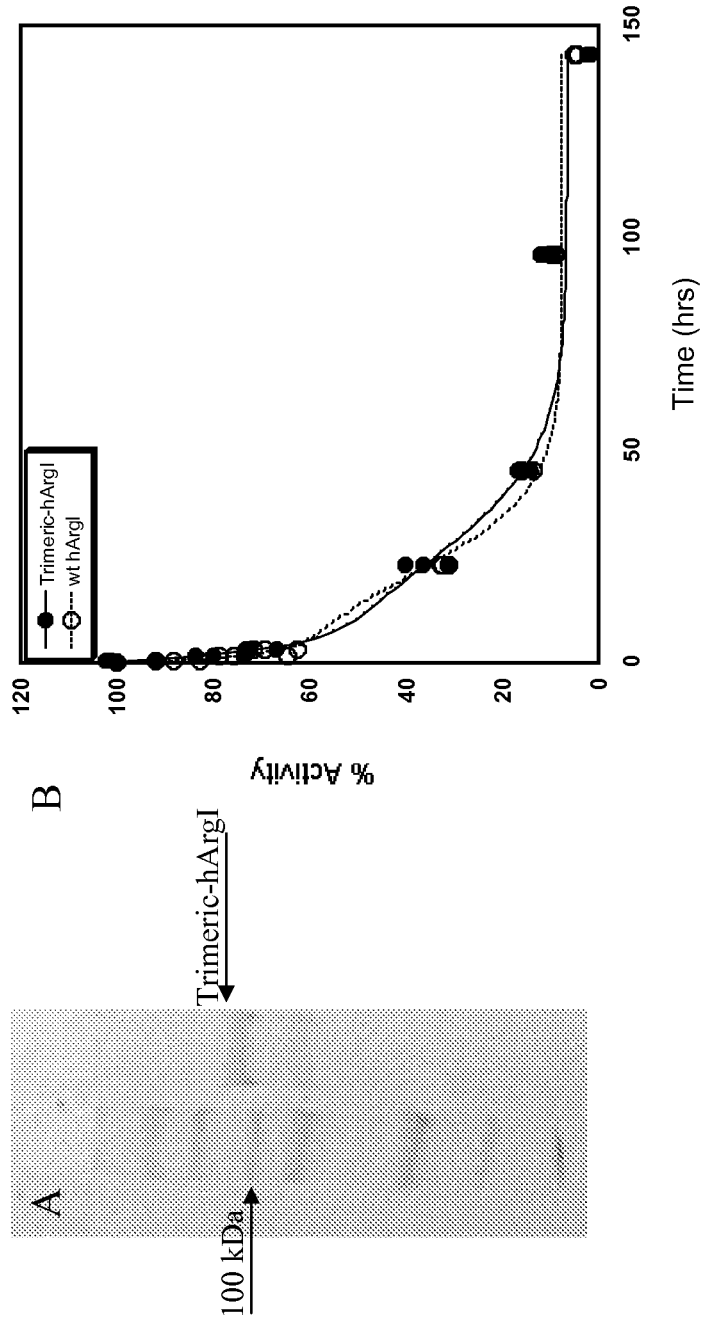
FIGS. 3A-B.

The trimeric-hArgI is then purified essentially as described in Example 1 and shows an apparent MW of ~110 kDa (FIG. 3A).

Example 4

Steady State Kinetics of Peg20K-hArgI and Trimeric-hArgI

The inventors used the diacetylmonoxine (DAMO) derivitization of either urea products in the presence of strong acids, thiosemicarbazide, and $Fe^{3+}$ with heating to produce a chromophore with a $\lambda_{max}$ of ~530 nm. The dye structure is not definitively known, but the reaction is hypothesized to be a condensation of DAMO and urea/uriedo that is possibly stabilized by $Fe^{3+}$ ions (Beale and Croft, 1961). The inventors constructed a standard curve of urea vs. $A_{530}$ that was found to be linear between 0-300 μM urea with a lower detection limit of 1-2 μM. The steady-state kinetics of Peg20K-hArgI and Trimeric-hArgI were examined over a range of L-arginine concentrations (0-2 mM) in a 100 mM Hepes buffer pH 7.4, 37° C. Typically reactions were performed by equilibrating 1.5 ml eppendorf tubes containing 200 μL of substrate at 37° C. in a heat block, starting the reaction by adding 5 μL of enzyme for 30 s and quenching with 15 μL of 12 N HCl. Reactions and blanks were then mixed with 800 μL of color developing reagent (COLDER) (Knipp and Vasak, 2000) and boiled for 15 min. After cooling for 10 min the samples were transferred to cuvettes and read at 530 nm on a spectrophotometer. L-arginine has a background absorbance that makes correction necessary, so L-arginine blanks were included for all concentrations used. The resulting data is then corrected for background, and the concentrations of product formed calculated from the standard curve. The product is then divided by the time and the concentration of enzyme used and $v_o/[E]$ is plotted vs. substrate concentration and fit directly to the Michaelis-Menten equation using software from Kaleidagrah. Fits to the data for hydrolysis of L-Arginine with Peg20K-hArgI resulted in a $k_{cat}$ of 290±5 s$^{-1}$, a $K_M$ of 0.16±0.01 mM and a $k_{cat}/K_M$ of 1,800±140 mM$^{-1}$ s$^{-1}$. Similarly, trimeric-hArgI yielded a $k_{cat}$ of 290±5 s$^{-1}$, a $K_M$ of 0.13±0.01 mM and a $k_{cat}/K_M$ of 2,200±200 mM$^{-1}$ s$^{-1}$.

Example 5

Serum Stability of Peg20K-hArgI and Trimeric-hArgI

Enzymes were added to pooled human serum (Innovative) at a concentration of 1 μM and incubated at 37° C. At various time points, aliquots were withdrawn and tested in triplicate for their ability to hydrolyze a concentration of L-Arg (1 mM). Data were plotted as percent activity vs. time and fit to a biphasic decay model (Equation 1) to calculate $T_{1/2}$ values (Where y=v at a given time, $y_{max}$=v at time 0, $y_{mid}$=v at end of the first loss of activity, $y_{min}$=v at the end of the experiment, k is an exponential rate, m is a Hill slope coefficient, $T_{0.5}$=time ½, and τ=time.

$$y = (y_{max} - y_{mid})e^{(-kt)} + \frac{(y_{mid} - y_{min})}{(1 + e^{(-m(T_{0.5}-t))})} + y_{min} \qquad \text{(Equation 1)}$$

Both trimeric-hArgI and Peg20K-hArgI display virtually identical stability to wt-hArgI displaying biphasic deactivation kinetics with a first half life of ~7 hrs and sequential half lives of 30-35 hrs. FIG. 3B shows a comparison of wt-hArgI and trimeric-hArgI.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 5,889,155
U.S. Appln. Ser. 61/110,218
Ausubel et al., Current Protocols in Molecular Biology, Greene Publishing Associates and Wiley Interscience, N.Y., 1994.
Beale and Croft, J. Clin. Pathol., 14:418-424, 1961.
Cellarier et al., Cancer Treat. Rev., 29:489-499, 2003.
Cheng et al., Cancer Lett., 224:67-80, 2005.
Cheng et al., Cancer Res., 67:4869-4877, 2007.
Dillon et al., Med. Sci. Monit., 8:BR248-253, 2002.
Dinndorf et al., Oncologist, 12:991-998, 2007.
Ensor et al., Cancer Res., 62:5443-5450, 2002.
Feun et al., J. Neurooncol., 82:177-181, 2007.
Harkki et al., BioTechnology, 7:596-603, 1989.
Hopwood et al., In: Genetic Manipulation of Streptomyces, A Laboratory Manual, The John Innes Foundation, Norwich, Conn., 1985.
Izzo et al., J. Clin. Oncol., 22:1815-1822, 2004.
Knipp and Vasak, Anal. Biochem., 286:257-264, 2000.
Lamb et al., Experimental Cell Res., 225:238-249, 2000.
Lopez et al., Febs J., 272:4540-4548, 2005.
Lordanescu, J. Bacteriol, 12:597 601, 1975.
Malumbres & Barbacid, Nature Rev., 1:222-231, 2001.
Maniatis, et al., Molecular Cloning, A Laboratory Manual, Cold Spring Harbor Press, Cold Spring Harbor, N.Y., 1988.
Mellor et al., Gene, 24:1-14, 1983.
Penttila et al., Gene, 61:155-164, 1987.
Remington's Pharmaceutical Sciences, 18th Ed. Mack Printing Company, 1289-1329, 1990.
Sabio et al., FEBS Lett., 501:161-165, 2001.
Savoca et al., Cancer Biochem. Biophys., 7:261-268.
Scott et al., Br. J. Cancer, 83:800-810, 2000.
Scott et al., Br. J. Cancer, 83:800-810, 2000.
Shen et al., Cancer Lett., 231:30-35, 2006.
Sibakov et al., Eur. J. Biochem., 145:567 572, 1984.
Storr & Burton, Br. J. Cancer, 30:50-59, 1974.
Ward, Proc, Embo-Alko Workshop on Molecular Biology of Filamentous Fungi, Helsinki, 119-128, 1989.
Wawrzynczak & Thorpe, In: Immunoconjugates, Antibody Conjugates In Radioimaging And Therapy Of Cancer, Vogel (Ed.), NY, Oxford University Press, 28, 1987.
Wetzler et al., Blood, 109:4164-4167, 2007.
Wheatley and Campbell, Pathol. Oncol. Res., 8:18-25, 2002.
Wheatley et al., Cellular Physiol. Biochem., 10:37-55, 2000.
Yoon et al., Int. J. Cancer, 120:897-905, 2007.

The invention claimed is:

1. A method for separating pegylated arginase from unpegylated arginase, comprising:
   a) obtaining a protein solution comprising pegylated arginase and unpegylated arginase; and
   b) separating the pegylated arginase by size from the unpegylated arginase at a pH from about 3 to about 5.5.

2. The method of claim 1, wherein the pegylated arginase is further defined as pegylated human arginase.

3. The method of claim 2, wherein the pegylated arginase is further defined as pegylated human arginase I.

4. The method of claim 2, wherein the pegylated arginase is further defined as pegylated human arginase II.

5. The method of claim 1, wherein the pegylated arginase is pegylated at an engineered cysteine residue.

6. The method of claim 1, wherein the pegylated arginase comprises cobalt as its metal cofactor.

7. The method of claim 1, wherein the pegylated arginase is separated from the unpegylated arginase by size exclusion chromatography.

8. The method of claim 1, wherein the pegylated arginase is separated from the unpegylated arginase at a pH from about 3.5 to about 5.0.

9. The method of claim 8, wherein the pegylated arginase is separated from the unpegylated arginase at a pH of about 4.5.

* * * * *

UNITED STATES PATENT AND TRADEMARK OFFICE
CERTIFICATE OF CORRECTION

PATENT NO. : 8,679,479 B2  
APPLICATION NO. : 13/380776  
DATED : March 25, 2014  
INVENTOR(S) : George Georgiou and Everett Stone Page 1 of 1

It is certified that error appears in the above-identified patent and that said Letters Patent is hereby corrected as shown below:

In title page, item (56) References Cited - Other Publications, delete the 5th reference on page 1 "Cheng et al., "pegylated recombinant human arginase (rhArg-pegs5,000mw) inhibits the in vitro and in vivo proliferation of human hepatocellular carcinoma through arginine depletion," Cancer Res., 67(1):309-317, 2007." and replace with --Cheng et al., "pegylated recombinant human arginase (rhArg-peg5,000mw) inhibits the in vitro and in vivo proliferation of human hepatocellular carcinoma through arginine depletion," Cancer Res., 67(1):309-317, 2007.-- therefor.

In title page, item (56) References Cited - Other Publications, delete the 9th reference on page 2 "Wheatley at al., "Single amino acid (arginine) restriction: growth and death of cultured HeLa and human diploid fibroblasts," Cellular Physiol. Biochem., 10:37-55, 2000." and replace with --Wheatley et al., "Single amino acid (arginine) restriction: growth and death of cultured HeLa and human diploid fibroblasts," Cellular Physiol. Biochem., 10:37-55, 2000.-- therefor.

Signed and Sealed this  
Third Day of June, 2014

Michelle K. Lee  
*Deputy Director of the United States Patent and Trademark Office*